United States Patent [19]

Hirose et al.

[11] Patent Number: 5,411,979

[45] Date of Patent: May 2, 1995

[54] OXAZOLINE DERIVATIVE, ITS PRODUCTION AND ITS USE

[75] Inventors: Taro Hirose; Hirosi Kisida; Shigeru Saito, all of Takarazuka; Hiroaki Fujimoto, Toyonaka, all of Japan

[73] Assignee: Sumitomo Chemical Company, Limited, Osaka, Japan

[21] Appl. No.: 10,015

[22] Filed: Jan. 27, 1993

[30] Foreign Application Priority Data

Jan. 28, 1992 [JP] Japan ................... 4-012967

[51] Int. Cl.6 .............................. A01N 43/76
[52] U.S. Cl. .................... 514/374; 514/340; 546/275; 548/237; 548/239
[58] Field of Search ............ 548/237, 238, 239; 514/374

[56] References Cited

U.S. PATENT DOCUMENTS

| | | | |
|---|---|---|---|
| 4,702,864 | 10/1987 | Magolda et al. | 558/170 |
| 4,977,171 | 12/1990 | Suzuki et al. | 514/374 |
| 5,141,948 | 8/1992 | Miyamoto et al. | 514/374 |
| 5,210,206 | 5/1993 | Morton | 548/238 |

FOREIGN PATENT DOCUMENTS

| | | |
|---|---|---|
| 345775A1 | 12/1989 | European Pat. Off. . |
| 432661A2 | 6/1991 | European Pat. Off. . |
| 02304069 | 12/1990 | Japan . |
| 0489484 | 3/1992 | Japan . |

OTHER PUBLICATIONS

Atmani et al. Synthetic, Communications vol. 21 (No. 22) pp. 2283–2290 (1991).

Chemical Abstracts, vol. 117, No. 3, Jul. 20, 1992, Columbus, Ohio, US; Abstract No. 27066x, A. Atmani et al, "From oxazolines to precursors of amino acids", p. 777.

*Primary Examiner*—Donald G. Daus
*Attorney, Agent, or Firm*—Sughrue, Mion, Zinn, Macpeak & Seas

[57] ABSTRACT

An oxazoline derivative having the formula:

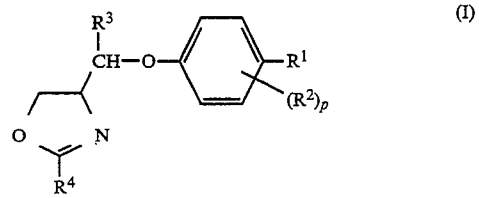

(I)

which is useful for control of insects, mites and/or ticks. $R_1$ is H, halo, (halo) alkyl, alkoxy alkyl, (halo) alkoxy alkyl, (halo) alkyl thio, (halo) cycloalkyl, alkylcycloalkyl, (halo) cycloalkoxy, alkylcycloalkoxy or ($R^5$) phenyl, phenoxyl or phenylthio or ($R^5$) pyridyl, pyridoxyl or pyridylthio, $R_3$ is H or methyl, $R_4$ is phenyl or mono or disubstituted phenyl.

18 Claims, No Drawings

OXAZOLINE DERIVATIVE, ITS PRODUCTION AND ITS USE

The present invention relates to a novel oxazoline derivative having the formula:

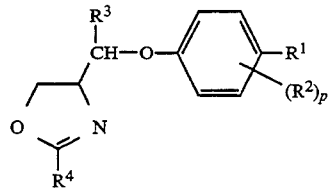
(I)

wherein $R^1$ is a hydrogen atom, a halogen atom, a $C_1$-$C_{16}$ alkyl group, a $C_1$-$C_{16}$ haloalkyl group, an alkoxyalkyl group having 2 to 16 carbon atoms, a $C_1$-$C_{16}$ alkoxy group, a $C_1$-$C_{16}$ haloalkoxy group, a $C_1$-$C_{16}$ alkylthio group, a $C_1$-$C_{16}$ haloalkylthio group, a $C_3$-$C_{16}$ cycloalkyl group, a $C_3$-$C_{16}$ halocycloalkyl group, an alkylcycloalkyl group having 4 to 16 carbon atoms, a $C_5$-$C_{16}$ cycloalkoxy group, a $C_5$-$C_{16}$ halocycloalkoxy group, an alkylcycloalkoxy group having 5 to 16 carbon atoms, or a group of the formula:

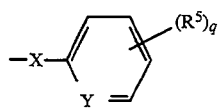

(wherein $R^5$ is, the same or different, a hydrogen atom, a halogen atom, a $C_1$-$C_8$ alkyl group, a $C_1$-$C_8$ haloalkyl group, an alkoxyalkyl group having 2 to 8 carbon atoms, a $C_1$-$C_8$ alkoxy group, a $C_1$-$C_8$ haloalkoxy group, a $C_1$-$C_8$ alkylthio group or a $C_1$-$C_8$ haloalkylthio group; X is a single bond, an oxygen atom, a sulfur atom, a methylene group or a methyleneoxy group (—$CH_2O$—, —$OCH_2$—); Y is a methine (—CH═) or a nitrogen atom (—N═); q is an integer of 1 to 5); $R^2$ is a hydrogen atom, a halogen atom, a $C_1$-$C_3$ alkyl group, a $C_1$-$C_3$ alkoxy group or a $C_1$-$C_3$ alkylthio group; p is an integer of 1 to 4; $R^3$ is a hydrogen atom or a methyl group; and $R^4$ is a group of the formula:

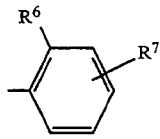

(wherein $R^6$ and $R^7$ may be the same or different, and each of which is a hydrogen atom, a halogen atom, a $C_1$-$C_3$ alkyl group, a $C_1$-$C_3$ haloalkyl group, a $C_1$-$C_3$ alkoxy group or a $C_1$-$C_3$ haloalkoxy group), a process for producing the same, its intermediate, and insecticides and/or acaricides containing the same as an active ingredient.

It is described in European Patent Specification No. 345,775 and No. 432,661 that a certain oxazoline derivative is useful as an active ingredient of insecticide and/or acaricide.

As a result of extensive investigations of compounds having an excellent insecticidal and acaricidal effect and an excellent resistance to sunlight, the present inventors have found that an oxazoline derivative having the formula (I) exhibits an extremely high insecticidal and acaricidal effect, and thus have accomplished the present invention.

According to the present invention, there is provided an oxazoline derivative having the formula:

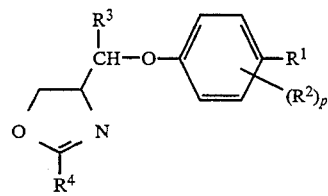
(I)

wherein $R^1$ is a hydrogen atom, a halogen atom, a $C_1$-$C_{16}$ alkyl group, a $C_1$-$C_{16}$ haloalkyl group, an alkoxyalkyl group having 2 to 16 carbon atoms, a $C_1$-$C_{16}$ alkoxy group, a $C_1$-$C_{16}$ haloalkoxy group, a $C_1$-$C_{16}$ alkylthio group, a $C_1$-$C_{16}$ haloalkylthio group, a $C_3$-$C_{16}$ cycloalkyl group, a $C_3$-$C_{16}$ halocycloalkyl group, an alkylcycloalkyl group having 4 to 16 carbon atoms, a $C_5$-$C_{16}$ cycloalkoxy group, a $C_5$ -$C_{16}$ halocycloalkoxy group, an alkylcycloalkoxy group having 5 to 16 carbon atoms, or a group of the formula:

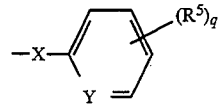

(wherein $R^5$ is, the same or different, a hydrogen atom, a halogen atom, a $C_1$-$C_8$ alkyl group, a $C_1$-$C_8$ haloalkyl group, an alkoxyalkyl group having 2 to 8 carbon atoms, a $C_1$-$C_8$ alkoxy group, a $C_1$-$C_8$ haloalkoxy group, a $C_1$-$C_8$ alkylthio group or a $C_1$-$C_8$ haloalkylthio group; X is a single bond, an oxygen atom, a sulfur atom, a methylene group or a methyleneoxy group (—$CH_2O$—, —$OCH_2$—); Y is a methine (—CH═) or a nitrogen atom (—N═); q is an integer of 1 to 5); $R^2$ is a hydrogen atom, a halogen atom, a $C_1$-$C_3$ alkyl group, a $C_1$-$C_3$ alkoxy group or a $C_1$-$C_3$ alkylthio group; p is an integer of 1 to 4; $R^3$ is a hydrogen atom or a methyl group; and $R^4$ is a group of the formula:

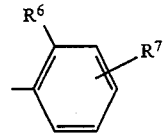

(wherein $R^6$ and $R^7$ may be the same or different and each of which is a hydrogen atom, a halogen atom, a $C_1$-$C_3$ alkyl group, a $C_1$-$C_3$ haloalkyl group, a $C_1$-$C_3$ alkoxy group or a $C_1$-$C_3$ haloalkoxy group), a process for producing the same, its intermediate, and insecticides and/or acaricides containing the same as an active ingredient.

Hereinafter, the present invention is explained in detail.

In the oxazoline derivative (I), examples of the halogen atom are a fluorine atom, a chlorine atom, a bromine atom and an iodine atom, preferably a fluorine atom or a chlorine atom.

Examples of the $C_1$-$C_{16}$ alkyl part contained in the $C_1$-$C_{16}$ alkyl group, the $C_1$-$C_{16}$ haloalkyl group, the $C_1$-$C_{16}$ alkoxy group, the haloalkoxy group, the $C_1$–$C_{16}$ alkylthio group and the $C_1$–$C_{16}$ haloalkylthio group represented by $R^1$ are methyl, ethyl, propyl, 1-methylethyl, butyl, 2-methylpropyl, 1-methylpropyl, 1,1-dimethylethyl, pentyl, 3-methylbutyl, 1,1-dimethylpropyl, 2,2-dimethylpropyl, hexyl, heptyl, octyl, decyl, dodecyl, tetradecyl, hexadecyl, etc.

Examples of the $C_1$–$C_{16}$ haloalkyl part, which is particularly preferred among the above-mentioned haloalkyl, haloalkoxy and haloalkylthio groups are difluoromethyl, trifluoromethyl, 2,2,2-trifluoroethyl, 1,1,2,2-tetrafluoroethyl, 2-chloro-1,1,2-trifluoroethyl, 2,2-dichloro-1,1-difluoroethyl, 1,1,2,2,2-pentafluoroethyl, 2-bromo-1,1,2,2-tetrafluoroethyl, 2-chloro-1,1,2,2-tetrafluoroethyl, 2,2,3,3,3-pentafluoropropyl, 1,1,2,2,3,3,3-heptafluoropropyl, 1,1,2,3,3,3-hexafluoropropyl, 10-fluorodecyl, 10-bromodecyl, 13-fluorotridecyl, 13-bromotridecyl, 16-fluorohexadecyl, 16-bromohexadecyl, etc.

Examples of the alkoxyalkyl group having 2 to 16 carbon atoms represented by $R^1$ are 2-methoxyethyl, 2-ethoxyethyl, 2-propyloxyethyl, 2-butyloxyethyl, 2-pentyloxyethyl, 2-(1-methylethoxy)ethyl, 2-hexyloxyethyl, 2-decyloxyethyl, 2-tetradecyloxyethyl, 4-ethyloxybutyl, 4-butyloxybutyl, 4-decyloxybutyl, 4-dodecyloxybutyl, etc.

Examples of the $C_3$–$C_{16}$ cycloalkyl group and the $C_3$–$C_{16}$ halocycloalkyl group represented by $R^1$ are cyclopropyl, cyclopentyl, cyclohexyl, cycloheptyl, cyclodecyl, 3-fluorocyclopentyl, 3-chlorocyclopentyl, 3-bromocyclopentyl, 2-chlorocyclohexyl, 4-chlorocycloheptyl, etc. The preferred examples are those groups which have 3 to 10 carbon atoms.

Examples of the alkylcycloalkyl group having 4 to 16 carbon atoms, represented by $R^1$ are 1-methylcyclopropyl, 4-methylcyclohexyl, 4-(1,1-dimethylethyl)cyclohexyl, 4-[1-(1,1-dimethyl)butyl]cyclohexyl, 4-[1-(3,7-dimethyl)octyl]cyclohexyl, etc.

Examples of the $C_5$–$C_{16}$ cycloalkoxy group and the $C_5$–$C_{16}$ halocycloalkoxy group represented by $R^1$ are cyclopentyloxy, cyclohexyloxy, 2-chlorohexyloxy, cycloheptyloxy, cyclodecyloxy, 3-fluoropentyloxy, 3-chloropentyloxy, 3-bromopentyloxy, 4-chlorocycloheptyloxy, etc. The preferred examples are those groups which have 3 to 10 carbon atoms.

Examples of the alkylcycloalkoxy group having 5 to 16 carbon atoms represented by $R^1$ are 4-methylcyclohexyloxy, 4-(1,1-dimethylethyl)cyclohexyloxy, 4-[1-(1,1-dimethyl)butyl]cyclohexyloxy, 4-[1-(3,7-dimethyl)octyl]cyclohexyloxy, etc.

Examples of $C_1$–$C_8$ alkyl part contained in the $C_1$–$C_8$ alkyl group, the $C_1$–$C_8$ haloalkyl group, the $C_1$–$C_8$ alkoxy group, the $C_1$–$C_8$ haloalkoxy group, the $C_1$–$C_8$ alkylthio group and the $C_1$–$C_8$ haloalkylthio group represented by $R^5$ are methyl, ethyl, propyl, 1-methylethyl, butyl, 2-methylpropyl, 1-methylbutyl, 1,1-dimethylethyl, pentyl, 3-methylbutyl, 1-methylbutyl, 1,1-dimethylpropyl, 2,2-dimethylpropyl, hexyl, heptyl, octyl, etc. Examples of the $C_1$–$C_8$ haloalkyl part which are particularly preferred among the above-mentioned $C_1$–$C_8$ haloalkyl, $C_1$–$C_8$ haloalkoxy and $C_1$–$C_8$ haloalkylthio group are difluoromethyl, trifluoromethyl, 1,1,2,2-tetrafluoroethyl, 2,2,2-trifluoroethyl, 2-chloro-1,1,2-trifluoroethyl, 2-bromo-1,1,2-trifluoroethyl, 1,1,2,2,2-pentafluoroethyl, 1,1,2,3,3,3-hexafluoropropyl, 2,2,3,3,3-pentafluoropropyl, 1,1,2,2,3,3,3-heptafluoropropyl, 6-fluorohexyl, 8-fluorooctyl, etc. Examples of the alkoxyalkyl group having 2 to 8 carbon atoms, represented by $R^5$ are methoxymethyl, 2-methoxyethyl, 2-ethoxyethyl, 2-propyloxyethyl, 2-butyloxyethyl, 2-pentyloxyethyl, 2-(1-methylethoxy)ethyl, 2-hexyloxyethyl, etc.

Examples of the $C_1$–$C_3$ alkyl part contained in the $C_1$–$C_3$ alkyl group, the $C_1$–$C_3$ alkoxy group and the $C_1$–$C_3$ alkylthio group represented by $R^2$ are methyl, ethyl, propyl and 1-methylethyl.

Examples of the $C_1$–$C_3$ alkyl group and the $C_1$–$C_3$ haloalkyl group represented by $R^6$ or $R^7$ are methyl, ethyl, propyl, 1-methylethyl, difluoromethyl, trifluoromethyl, 3-chloropropyl, etc.

Examples of the $C_1$–$C_3$ alkoxy group and the $C_1$–$C_3$ haloalkoxy group represented by $R^6$ or $R^7$ are methoxy, ethoxy, propoxy, 1-methylethoxy, difluoromethoxy, trifluoromethoxy, 2,2,2-trifluoroethoxy, 1,1,2,2,2-pentafluoroethoxy, 1,1,2,2-tetrafluoroethoxy, 2-chloro-1,1,2-trifluoroethoxy, 2,2,3,3,3-pentafluoropropyl, 3-bromopropyl, etc.

Among the above $R^1$, there is preferred a group of the formula:

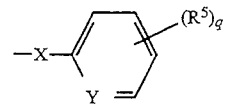

(wherein $R^5$ is, the same or different, a hydrogen atom, a halogen atom, a $C_1$–$C_8$ alkyl group, a $C_1$–$C_8$ haloalkyl group, an alkoxyalkyl group having 2 to 8 carbon atoms, a $C_1$–$C_8$ alkoxy group, a $C_1$–$C_8$ haloalkoxy group, a $C_1$–$C_8$ alkylthio group or a $C_1$–$C_8$ haloalkylthio group; X is a single bond, an oxygen atom, a sulfur atom, a methylene group or a methyleneoxy group (—CH$_2$O—, —OCH$_2$—); Y is a methine (—CH=) or a nitrogen atom (—N=); q is an integer of 1 to 5), and more preferred a group of the formula:

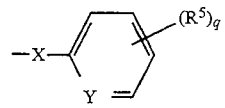

(wherein $R^5$ is a hydrogen atom, a halogen atom, a $C_1$–$C_8$ alkyl group, a $C_1$–$C_8$ haloalkyl group, a $C_1$–$C_8$ alkoxy group or a $C_1$–$C_8$ haloalkoxy group at the p-position on the benzene ring to the substituent "X", X is a single bond or an oxygen atom; Y is a methine (—CH=); q is one).

Among the above $R^3$, a hydrogen atom is preferred.

Among the above $R^4$, there is preferred a group substituted by $R^7$ at the 6-position on the benzene ring, namely, a phenyl group substituted by $R^6$ at the 2-position and $R^7$ at the 6-position on the benzene ring, and further $R^6$ and $R^7$ are preferably the same or different and each of which is a hydrogen atom or a halogen atom, more preferably a halogen atom and most preferably a fluorine atom.

Among the oxazoline derivatives (I), preferred are those wherein $R^1$ is a group of the formula:

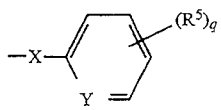

(wherein $R^5$ is, the same or different, a hydrogen atom, a halogen atom, a $C_1$-$C_8$ alkyl group, a $C_1$-$C_8$ haloalkyl group, a $C_1$-$C_8$ alkoxy group, a $C_1$-$C_8$ haloalkoxy group or a $C_1$-$C_8$ alkylthio group; X is a single bond, an oxygen atom or a methylene group; Y is a methine (—CH=) or a nitrogen atom; q is an integer of 1 or 2; $R^2$ is a hydrogen atom, a halogen atom, a $C_1$-$C_3$ alkyl group or a $C_1$-$C_3$ alkoxy group; p is an integer of 1 to 3; $R^3$ is a hydrogen atom; $R^4$ is a group of the formula:

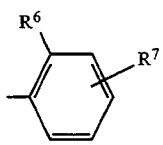

(wherein $R^6$ and $R^7$ may be the same or different, and each of which is a halogen atom).

More preferred are those wherein $R^1$ is a group of the formula:

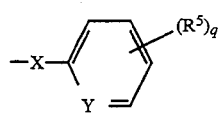

(wherein $R^5$ is a hydrogen atom, a halogen atom, a $C_1$-$C_8$ alkyl group, a $C_1$-$C_8$ haloalkyl group, a $C_1$-$C_8$ alkoxy group or a $C_1$-$C_8$ haloalkoxy group at the p-position on the benzene ring to the substituent "X"; X is a single bond or an oxygen atom; Y is a methine (—CH=); q is one); $R^2$ is a hydrogen atom, a halogen atom, a $C_1$-$C_3$ alkyl group or a $C_1$-$C_3$ alkoxy group; p is an integer of 1 to 3; $R^3$ is a hydrogen atom; $R^4$ is a group of the formula:

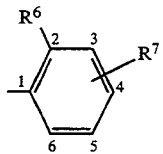

(wherein $R^7$ is at the 6-position on the benzene ring and $R^6$ and $R^7$ may be the same or different, and each of which is a halogen atom, and particularly preferably a fluorine atom).

The oxazoline derivative (I) is produced by reacting an aminoalcohol compound of the formula:

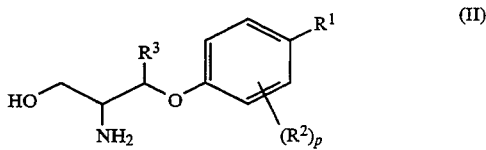

wherein $R^1$, $R^2$, $R^3$ and p are each as defined above with a carboxylic acid derivative of the formula:

wherein $R^4$ is as defined above and $L^1$ is a hydroxyl group or a halogen atom.

(i) When the carboxylic acid derivative (III) is one wherein $L^1$ is a hydroxyl group, the above reaction may be carried out usually in an inert solvent in the presence of a dehydrating agent at a temperature of from about 60° C. to the boiling point of the solvent for from about 1 to about 50 hours.

The molar proportion of the aminoalcohol compound (II) to the carboxylic acid derivative (III) to be used for the reaction is not limitative, but is preferably from 2:1 to 1:2.

The amount of the dehydrating agent is not limitative but it is preferably from one to one hundred equivalents per equivalent of the aminoalcohol compound (II).

Examples of the inert solvent are aromatic hydrocarbons such as benzene, toluene, xylene, chlorobenzene, dichlorobenzene, nitrobenzene, etc.

Examples of the dehydrating agent are sulfuric acid, phosphorus pentaoxide, polyphosphoric acid, etc.

After completion of the reaction, post-treatment follows in a conventional manner such as extraction with an organic solvent, concentration, etc. If necessary and desired, the product may be further purified by chromatography, distillation, recrystallization, etc.

(ii) When the carboxylic acid derivative (III) is one wherein $L^1$ is a halogen atom, the above reaction is carried out via an amide compound of the formula:

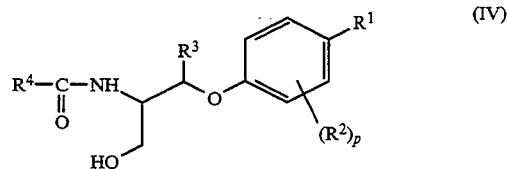

wherein $R^1$, $R^2$, $R^3$, $R^4$ and p are each as defined above.

Namely, the oxazoline derivative (I) is produced by:

(A) reacting the aminoalcohol compound (II) with the carboxylic acid derivative (III) in the presence of a base to obtain the amide compound (IV) (referred to hereinafter as "Step A") and (B) subjecting the amide compound (IV) to cyclization in the presence of a dehydrating agent (referred to hereinafter as "Step B").

The above "Step A" may be carried out usually in an inert solvent at a temperature of from about −10° C. to about 50° C. for from about 1 to about 30 hours.

The molar proportion of the aminoalcohol compound (II) to the carboxylic acid derivative (III) to be used for the reaction is not limitative, but is preferably from 2:1 to 1:2.

The amount of the base is not limitative, but is preferably from one to five equivalents per equivalent of the aminoalcohol compound (II).

Examples of the inert solvent are alcohols such as methanol, ethanol, isopropyl alcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-heptane, petroleum ether, etc.; water; and mixtures thereof.

Examples of the base are inorganic bases such as sodium hydroxide, potassium hydroxide, sodium carbonate, etc. and organic bases such as triethylamine, pyridine, N,N-diethylaniline, etc.

After completion of the reaction, post-treatment follows in a conventional manner such as extraction with an organic solvent, concentration, etc. If necessary and desired, the product may be further purified by chromatography, distillation, recrystallization, etc.

The above "Step B" may be carried out usually in an inert solvent at a temperature of from about 60° C. to the boiling point of the solvent for from about 1 to about 50 hours.

The amount of the dehydrating agent is not limitative, but it is preferably from one to one hundred equivalents per equivalent of the amide compound (IV).

Examples of the inert solvent are aromatic hydrocarbons such as benzene, toluene, xylene, chlorobenzene, dichlorobenzene, etc. and mixtures thereof.

Examples of the dehydrating agent are sulfuric acid, phosphorus pentaoxide, polyphosphoric acid, etc.

After completion of the reaction, post-treatment follows in a conventional manner such as extraction with an organic solvent, concentration, etc. If necessary and desired, the product may be further purified by chromatography, distillation, recrystallization, etc.

Furthermore, the oxazoline derivative (I) is produced by:

(C) reacting the amide compound (IV) with a halogenating agent to obtain a haloamide compound of the formula:

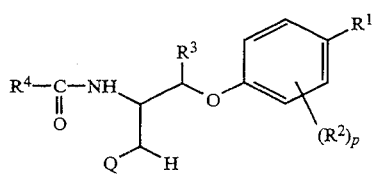

(V)

wherein $R^1$, $R^2$, $R^3$, $R^4$ and p are each as defined above and Q is a halogen atom (referred to hereinafter as "Step C") and (D) subjecting the haloamide compound (V) to cyclization in the presence of a base (referred to hereinafter as "Step D").

The above "Step C" may be carried out usually in an inert solvent at a temperature of from about $-10°$ C. to the boiling point of the solvent for from about 1 to about 10 hours.

The amount of the halogenating agent is not limitative, but it is preferably from one to ten equivalents per equivalent of the amide compound.

Examples of the inert solvent are aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc. and mixtures thereof.

Examples of the halogenating agent are thionyl chloride, phosphorus oxychloride, phosphorus trichloride, phosphorus tribromide, etc.

After completion of the reaction, post-treatment follows in a conventional manner such as extraction with an organic solvent, concentration, etc. If necessary and desired, the product may be further purified by chromatography, distillation, recrystallization, etc.

The above "Step D" may be carried out usually in an inert solvent at a temperature of from about 0° C. to about 110° C. for from about 0.5 to about 5 hours.

The amount of the base is not limitative but it is preferably from one to ten equivalents per equivalent of the haloamide compound.

Examples of the inert solvent are alcohols such as methanol, ethanol, isopropyl alcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-heptane, petroleum ether, etc.; water; and mixtures thereof.

Examples of the base are inorganic bases such as sodium hydroxide, potassium hydroxide, sodium carbonate, calcium hydroxide, etc. and organic bases such as triethylamine, pyridine, N,N-dimethylaniline, 4-N,N-dimethylaminopyridine, etc.

After completion of the reaction, post-treatment follows in a conventional manner such as extraction with an organic solvent, concentration, etc. If necessary and desired, the product may be further purified by chromatography, distillation, recrystallization, etc.

Among the starting compounds in the above processes, the aminoalcohol compound (II) is obtainable from appropriate commercial products by a conventional procedure as shown below.

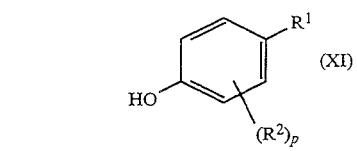

"A phenol compound"

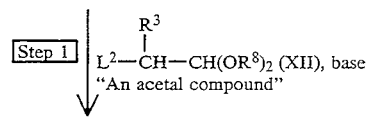

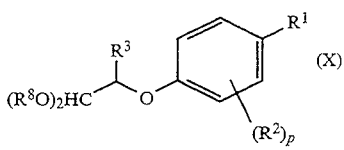

"An ether compound"

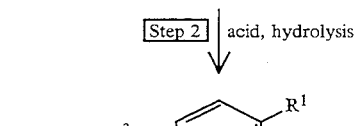

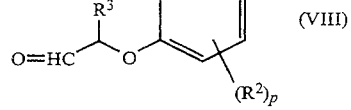

"An aldehyde compound"

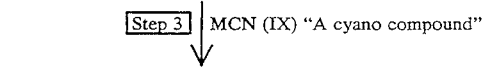

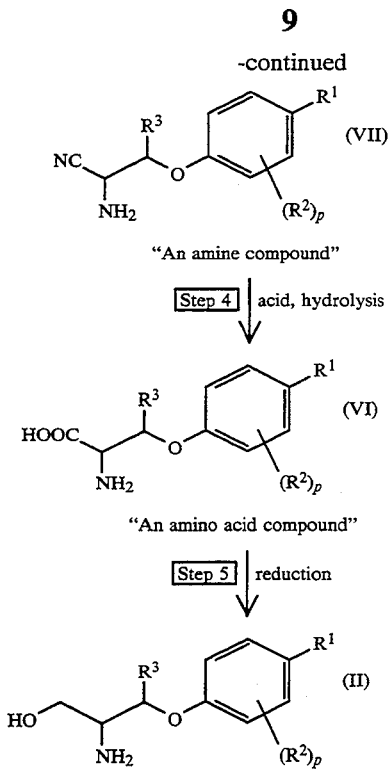

-continued

"An amine compound"

Step 4 | acid, hydrolysis

"An amino acid compound"

Step 5 | reduction wherein $R^1$, $R^2$, $R^3$ and p are each as defined above; $R^8$ is a lower alkyl group; M is a hydrogen atom, a sodium atom or a potassium atom; $L^2$ is a halogen atom.

The above "Step 1" in which the ether compound (X) is produced from the phenol compound (XI) may be carried out usually in an inert solvent in the presence of a base at a temperature of from about 0° C. to about 150° C. for from about 0.5 to about 50 hours.

The molar proportion of the phenol compound (XI) to the ether compound (X) to be used for the reaction is not limitative, but is preferably from 1:1 to 1:3.

The amount of the base is not limitative, but it is preferably from one to five equivalents per equivalent of the phenol compound (XI).

Examples of the inert solvent are aromatic hydrocarbons such as benzene, toluene, xylene, chlorobenzene, dichlorobenzene, etc.; aliphatic hydrocarbons such as n-hexane, n-heptane, petroleum ether, etc.; halogenated hydrocarbons such dichloromethane, chloroform, 1,2-dichloroethane, etc.; ethers such as diethyl ether, tetrahydrofuran, dioxane, etc.; ketones such as acetone, methyl ethyl ketone, methyl isobutyl ketone, etc.; nitriles such as acetonitrile, etc.; nitro compounds such as nitrobenzene, etc.; polar solvents such as N,N-dimethylformamide, N,N-dimethylacetamide, dimethylsulfoxide, sulfolane, etc.; water; and mixtures thereof.

Examples of the base are alkaline metals such as sodium, potassium, etc.; alkaline metal hydrides such as sodium hydride, potassium hydride, etc.; alkaline metal hydroxides such as sodium hydroxide, potassium hydroxide, etc.; alkaline metal carbonates such as sodium carbonate, potassium carbonate, etc.; alkaline metal alkoxides such as sodium ethoxide, sodium methoxide, etc. When necessary or desired, an ammonium salt such as triethylbenzylammonium chloride or tetrabutylammonium bromide may be added to the reaction system as a catalyst.

Moreover, an alkaline metal salt of the phenol compound (XI) may also be used instead of the phenol compound (XI).

After completion of the reaction, post-treatment follows in a conventional manner such as extraction with an organic solvent, concentration, etc. If necessary and desired, the product may be further purified by chromatography, distillation, recrystallization, etc.

The above "Step 2" in which the aldehyde compound (VIII) is produced from the ether compound (X) may be carried out usually in an inert solvent in the presence of an acid at a temperature of from about −10° C. to about 50° C. for from about 0.5 to about 10 hours.

The amount of the acid is not limitative, but it is preferably from one to fifty equivalents per equivalent of the ether compound (X).

Examples of the inert solvent are carboxylic acids such as acetic acid, trifluoroacetic acid, etc.; alcohols such as methanol, ethanol, etc.; water; and mixtures thereof.

Examples of the acid are acetic acid, trifluoroacetic acid, hydrochloric acid, sulfuric acid, phosphoric acid, etc.

After completion of the reaction, post-treatment follows in a conventional manner such as extraction with an organic solvent, concentration, etc., however it is preferable to use the product in the next step as soon as possible for the reason that the aldehyde compound (VIII) is relatively unstable.

The above "Step 3" in which the amine compound (VII) is produced from the aldehyde compound (VIII) may be carried out usually in an inert solvent in the presence of ammonia at a temperature of from about −20° C. to about 50° C. for from about 0.5 to about 50 hours.

The molar proportion of the aldehyde compound (VIII) to the cyano compound (IX) to be used for the reaction is not limitative, but is preferably from 1:1 to 1:10.

The amount of the ammonia is not limitative, but it is preferably from one to excess equivalents per equivalent of the aldehyde compound (VIII).

Examples of the inert solvent are alcohols such as methanol, ethanol, etc.; water; and mixtures thereof.

When the cyano compound (IX) wherein M is a sodium atom or a potassium atom is used in the reaction, it may be preferable that the reaction to be carried out in the presence of an ammonium salt of a strong acid in an amount of from about one to excess equivalents per equivalent of the cyano compound (IX).

Examples of the ammonium salt of strong acid are ammonium chloride, etc.

After completion of the reaction, post-treatment follows in a conventional manner such as extraction with an organic solvent, concentration, etc. If necessary and desired, the product may be further purified by chromatography, distillation, recrystallization, etc.

The above "Step 4" in which the amino acid compound (VI) is produced from the amine compound (VII) may be carried out usually in an inert solvent such as water in the presence of an acid at a temperature of from about 30° C. to about 50° C. for from about 1 to about 50 hours.

The amount of the acid is not limitative, but it is preferably from 0.01 to 100 equivalents per equivalent of the amine compound (VII).

Examples of the acid are mineral acids such as hydrochloric acid, sulfuric acid, etc.

After completion of the reaction, the product may be obtained by deposition on cooling, filtration, etc.

The above "Step 5" in which the aminoalcohol compound (II) is produced from the amino acid compound (VI) may be carried out usually in an inert solvent in the presence of a reducing agent at a temperature of from about 0° C. to about 150° C. for from about 0.5 to about 30 hours.

The amount of the reducing agent is not limitative, but it is preferably from one to ten equivalents per equivalent of the amino acid compound (VI).

Examples of the inert solvent are ethers such as diethyl ether, tetrahydrofuran, dioxane, etc.; aromatic hydrocarbons such as benzene, toluene, xylene, etc.; and mixtures thereof.

Examples of the reducing agent are diisobutylaluminum hydride, aluminum hydride, lithium aluminum hydride, etc.

Moreover, the reaction "Step 5" may be also carried out as heterogeneous catalytic reduction with hydrogen gas in the presence of a catalyst such as ruthenium oxide, rhenium oxide, copper chromite, etc.

Furthermore, the oxazoline derivative (I) is also produced by reacting an oxazoline compound of the formula:

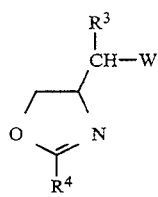
(XIII)

wherein $R^3$ and $R^4$ are each as defined above and W is a hydroxyl group, a halogen atom, a tosyloxy group or a mesyloxy group, with the phenol compound (XI).

(i) When the oxazoline compound (XIII) is one wherein W is a hydroxyl group, the above reaction may be carried out usually in an inert solvent in the presence of a dehydrating agent at a temperature of from about −50° C. to about 110° C. for from about 0.5 to about 100 hours.

The molar proportion of the oxazoline compound (XIII) to the phenol compound (XI) to be used for the reaction is not limitative, but is preferably from 2:1 to 1:10.

The amount of the dehydrating agent is not limitative, but it is preferably from 0.001 to 100 equivalents per equivalent of the oxazoline compound (XIII).

Examples of the inert solvent are ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; water; and mixtures thereof.

Examples of the dehydrating agent are dicyclohexylcarbodiimide, diethyl azodicarboxylate, diisopropyl azodicarboxylate, 1-ethyl-3-(3-dimethylaminopropyl)-carbodiimide hydrochloride, sulfuric acid, phosphorus pentaoxide, polyphosphoric acid, etc.

After completion of the reaction, post-treatment follows in a conventional manner such as extraction with an organic solvent, concentration, etc. If necessary and desired, the product may be further purified by chromatography, distillation, recrystallization, etc.

(ii) When the oxazoline compound (XIII) is one wherein W is a halogen atom, a tosyloxy group or a mesyloxy group, the above reaction may be carried out usually in an inert solvent in the presence of a base at a temperature of from about 0° C. to about 110° C. for from about 0.5 to about 500 hours.

The molar proportion of the oxazoline compound (XIII) to the phenol compound (XI) to be used for the reaction is not limitative, but is preferably from 2:1 to 1:10.

The amount of the base is not limitative, but it is preferably from 0.5 to 100 equivalents per equivalent of the oxazoline compound (XIII).

Examples of the inert solvent are alcohols such as methanol, ethanol, isopropyl alcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; water; and mixtures thereof.

Examples of the base are inorganic bases such as sodium hydroxide, potassium hydroxide, calcium hydroxide, sodium carbonate, potassium carbonate, sodium hydride, potassium hydride, etc. and organic bases such as triethylamine, pyridine, N,N-dimethylaniline, 4-N,N-dimethylaminopyridine, etc.

After completion of the reaction, post-treatment follows in a conventional manner such as extraction with an organic solvent, concentration, etc. If necessary and desired, the product may be further purified by chromatography, distillation, recrystallization, etc.

Among the starting compounds in the above processes, the oxazoline compound (XIII) is obtainable from appropriate commercial products by a conventional procedure as shown below.

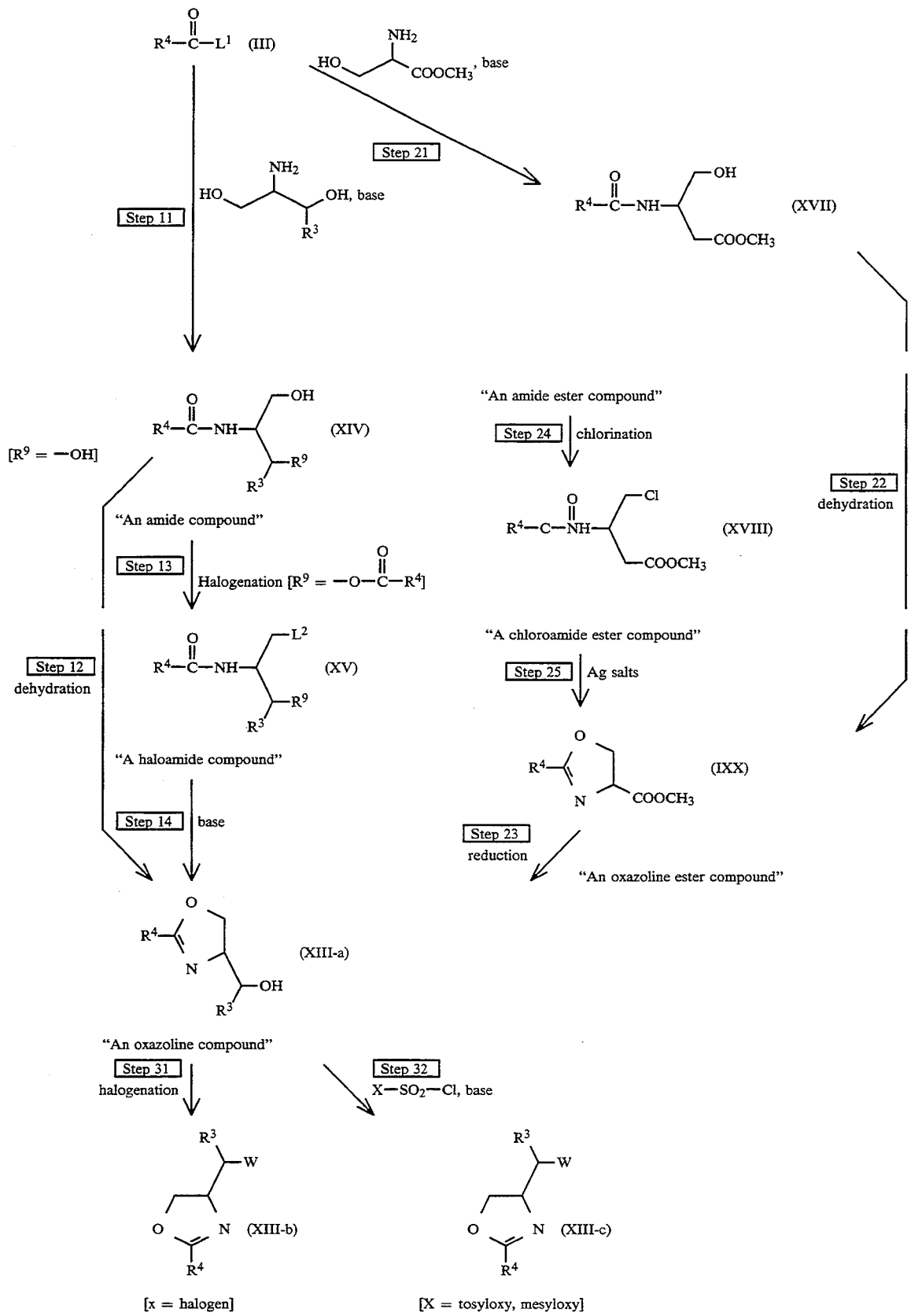
wherein $R^9$ is a hydroxyl group or a group of the formula:

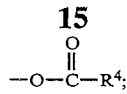

$R^3$, $R^4$, $L^1$, $L^2$ and W are each as defined above.

The above "Step 11" in which the amide compound (XIV) is produced from the carboxylic acid derivative (III) may be carried out usually in an inert solvent in the presence of a base at a temperature of from about −10° C. to about 50° C. for from about 1 to about 30 hours.

The molar proportion of 2-amino-1,3-propanediol to the carboxylic acid derivative (III) to be used for the reaction is not limitative, but is preferably from 2:1 to 1:4.

The amount of the base is not limitative, but it is preferably from 0.5 to 5 equivalents per equivalent of 2-amino-1,3-propanediol.

Examples of the inert solvent are alcohols such as methanol, ethanol, isopropylalcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; water; and mixtures thereof.

Examples of the base are inorganic bases such as sodium hydroxide, potassium hydroxide, sodium carbonate, potassium carbonate, sodium hydride, potassium hydride, etc. and organic bases such as triethylamine, pyridine, N,N-dimethylaniline, 4-N,N-dimethylaminopyridine, etc.

After completion of the reaction, post-treatment follows in a conventional manner such as extraction with an organic solvent, concentration, etc. If necessary and desired, the product may be further purified by chromatography, distillation, recrystallization, etc.

The above "Step 12" in which the oxazoline compound (XIII-a) is produced from the amide compound (XIV) wherein $R^9$ is a hydroxyl group may be carried out usually in an inert solvent in the presence of a dehydrating agent at a temperature of from about 60° C. to the boiling point of the solvent for from about 1 to about 50 hours.

The amount of the dehydrating agent is not limitative, but it is preferably from one to one hundred equivalents per equivalent of the amide compound (XIV) wherein $R^9$ is a hydroxyl group.

Examples of the inert solvent are aromatic hydrocarbons such as benzene, toluene, xylene, chlorobenzene, dichlorobenzene, etc. and mixtures thereof.

Examples of the dehydrating agent are sulfuric acid, phosphorus pentaoxide, polyphosphoric acid, etc.

After completion of the reaction, post-treatment follows in a conventional manner such as extraction with an organic solvent, concentration, etc. If necessary and desired, the product may be further purified by chromatography, distillation, recrystallization, etc.

The above "Step 13" in which the haloamide compound (XV) is produced from the amide compound (XIV) wherein $R^9$ is a group of the formula:

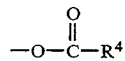

may be carried out usually in, or without, an inert solvent in the presence or absence of a halogenating agent at a temperature of from about −10° C. to about the boiling point of the solvent for from about 1 to about 10 hours.

The amount of the halogenating agent is not limitative, but it is preferably from one to one hundred equivalents per equivalent of the amide compound (XIV) wherein $R^9$ is a group of the formula:

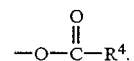

Examples of the inert solvent are aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; and mixtures thereof.

Examples of the halogenating agent are thionyl chloride, phosphorus oxychloride, phosphorus trichloride, phosphorus tribromide, etc.

After completion of the reaction, post-treatment follows in a conventional manner such as extraction with an organic solvent, concentration, etc. If necessary and desired, the product may be further purified by chromatography, distillation, recrystallization, etc.

The above "Step 14" in which the oxazoline compound (XIII-a) is produced from the haloamide compound (XV) wherein $R^9$ is a group of the formula:

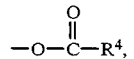

may be carried out usually in an inert solvent in the presence of a base at a temperature of from about 0° C. to about 10° C. for from about 0.5 to about 5 hours.

The amount of the base is not limitative, but it is preferably from one to one hundred equivalents per equivalent of the haloamide compound (XV) wherein $R^9$ is a group of the formula:

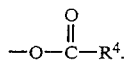

Examples of the inert solvent are alcohols such as methanol, ethanol, isopropyl alcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; water; and mixtures thereof.

Examples of the base are inorganic bases such as sodium hydroxide, potassium hydroxide, calcium hydroxide, sodium carbonate, potassium carbonate, sodium hydride, etc.

After completion of the reaction, post-treatment follows in a conventional manner such as extraction with an organic solvent, concentration, etc. If necessary and desired, the product may be further purified by chromatography, distillation, recrystallization, etc.

The above "Step 21" in which the amide ester compound (XVII) is produced from the carboxylic acid derivative (III) may be carried out usually in an inert solvent in the presence of a base at a temperature of from about −10° C. to about 50° C. for from about 1 to about 30 hours.

The molar proportion of the serine methyl ester to the carboxylic acid derivative (III) to be used for the reaction is not limitative, but is preferably from 2:1 to 1:4.

The amount of the base is not limitative, but it is preferably from 0.5 to 5 equivalents per equivalent of the carboxylic acid derivative (III).

Examples of the inert solvent are alcohols such as methanol, ethanol, isopropyl alcohol, n-butanol, etc.; ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc.; halogenated hydrocarbons such as dichloromethane, chloroform, carbon tetrachloride, 1,2-dichloroethane, etc.; aliphatic hydrocarbons such as n-hexane, n-pentane, n-heptane, petroleum ether, etc.; pyridine; water; and mixtures thereof.

Examples of the base are inorganic bases such as sodium hydroxide, potassium hydroxide, calcium hydroxide, sodium carbonate, potassium carbonate, sodium hydride, potassium hydride, etc. and organic bases such as triethylamine, pyridine, N,N-dimethylaniline, 4-N,N-dimethylaminopyridine, etc.

After completion of the reaction, post-treatment follows in a conventional manner such as extraction with an organic solvent, concentration, etc. If necessary and desired, the product may be further purified by chromatography, distillation, recrystallization, etc.

The above "Step 22" in which the oxazoline ester compound (IXX) is produced from the amide ester compound (XVII) may be carried out usually in an inert solvent in the presence of a dehydrating agent at a temperature of from about −50° C. to about 110° C. for from about 1 to about 50 hours.

The amount of the dehydrating agent is not limitative, but it is preferably from one to one hundred equivalents per equivalent of the amide ester compound (XVIII).

Examples of the inert solvent are benzene, toluene, xylene, chlorobenzene, dichlorobenzene, etc. and mixtures thereof.

Examples of the dehydrating agent are sulfuric acid, phosphorus pentaoxide, polyphosphoric acid, diethyl azodicarboxylate, dicyclohexylcarbodiimide, diisopropyl azodicarboxylate, 1-ethyl-3-(3-dimethylaminopropyl)carbodiimide hydrochloride, etc.

After completion of the reaction, post-treatment follows in a conventional manner such as extraction with an organic solvent, concentration, etc. If necessary and desired, the product may be further purified by chromatography, distillation, recrystallization, etc.

The above "Step 23" in which the oxazoline compound (XIII-a) is produced from the oxazoline ester compound (IXX) may be carried out usually in an inert solvent in the presence of a reducing agent at a temperature of from about −10° C. to about 100° C. for from about 0.5 to about 30 hours.

The amount of a reducing agent is not limitative, but it is preferably from one to ten equivalents per equivalent of the oxazoline ester compound (IXX).

Examples of the inert solvent are ethers such as diethyl ether, tetrahydrofuran, dioxane, diethylene glycol dimethyl ether, etc.; aromatic hydrocarbons such as benzene, toluene, xylene, chlorobenzene, dichlorobenzene, etc. and mixtures thereof.

Examples of the reducing agent are diisobutylaluminum hydride, aluminum hydride, lithium aluminum hydride, etc.

After completion of the reaction, post-treatment follows in a conventional manner such as extraction with an organic solvent, concentration, etc. If necessary and desired, the product may be further purified by chromatography, distillation, recrystallization, etc.

The above "Step 24" in which the chloroamide ester compound (XVIII) is produced from the amide ester compound (XVII) may be carried out usually in, or without, an inert solvent in the presence of a chlorinating agent at a temperature of from about −10° C. to the boiling point of the solvent for from about 1 to about 10 hours.

The amount of the chlorinating agent is not limitative, but it is preferably from one to one hundred equivalents per equivalent of the amide ester compound (XVII).

Examples of the inert solvent are aromatic hydrocarbons such as benzene, toluene, xylene, chlorobenzene, dichlorobenzene, etc.; halogenated hydrocarbons such as dichloromethane, chloroform, carbon tetrachloride, dichloroethane, etc.; aliphatic hydrocarbons such as n-hexane, n-pentane, n-heptane, petroleum ether, etc. and mixtures thereof.

Examples of the chlorinating agent are thionyl chloride, phosphorus oxychloride, phosphorus trichloride, etc.

After completion of the reaction, post-treatment follows in a conventional manner such as extraction with an organic solvent, concentration, etc. If necessary and desired, the product may be further purified by chromatography, distillation, recrystallization, etc.

The above "Step 25" in which the oxazoline ester compound (IXX) is produced from the chloroamide ester compound (XVIII) may be carried out usually in an inert solvent in the presence of a silver salt at a temperature of from about 0° C. to the boiling point of the solvent for from about 0.5 to about 100 hours.

The amount of the silver salt is not limitative, but it is preferably from one to one hundred equivalents per equivalent of the chloroamide ester compound (XVIII).

Examples of the inert solvent are aromatic hydrocarbons such as benzene, toluene, xylene, chlorobenzene, dichlorobenzene, etc.; aliphatic hydrocarbons such as n-hexane, n-pentane, n-heptane, petroleum ether, etc.; ethers such as diethyl ether, tetrahydrofuran, dioxane, diethylene glycol dimethyl ether, etc.

Examples of the silver salt are silver trifluoromethanesulfonate, silver acetate, silver carbonate, etc.

After completion of the reaction, post-treatment follows in a conventional manner such as extraction with an organic solvent, concentration, etc. If necessary and desired, the product may be further purified by chromatography, distillation, recrystallization, etc.

The above "Step 31" or "Step 32" in which the oxazoline compound (XIII-b) or the oxazoline compound (XIII-c) is produced from the oxazoline compound (XIII-a) can be carried out readily according to a conventional procedure such as halogenation and sulfonation.

After completion of the reaction, post-treatment follows in a conventional manner such as extraction with an organic solvent, concentration, etc. If necessary and desired, the product may be further purified by chromatography, distillation, recrystallization, etc.

When necessary or desired, an ammonium salt such as triethylbenzylammonium chloride or tetrabutylammonium bromide may be added to the reaction system as a catalyst.

Examples of the oxazoline derivatives (I) of the present invention are shown in Table 1.

The oxazoline derivatives (I) of the present invention have some asymmetric carbon atoms and can form optical isomers. Those optical isomers and their mixtures fall within the scope of the present invention.

TABLE 1

$$\begin{array}{c} R^3 \\ | \\ CH-O-\bigcirc-R^1 \\ | \\ \underset{O\diagdown\diagup N}{\overset{}{\underset{|}{C}}}\\ R^4 \end{array} \quad (R^2)_p$$

| $R^1$ | $(R^2)_p$ | $R^3$ | $R^4$ | |
|---|---|---|---|---|
| | | | $R^6$ | $R^7$ |
| t-$C_4H_9$ | H | H | F | 6-F |
| t-$C_4H_9$ | H | H | F | 6-Cl |
| t-$C_4H_9$ | H | H | Cl | H |
| t-$C_4H_9$ | H | H | H | H |
| t-$C_4H_9$ | H | H | Br | H |
| t-$C_4H_9$ | H | H | H | 4-F |
| t-$C_4H_9$ | H | H | H | 4-$CF_3$ |
| t-$C_4H_9$ | H | H | H | 4-$CH_3$ |
| t-$C_4H_9$ | H | H | H | 4-Cl |
| t-$C_4H_9$ | H | H | $CH_3$ | H |
| t-$C_4H_9$ | H | H | i-$C_3H_7$ | H |
| t-$C_4H_9$ | H | H | $CF_3$ | H |
| t-$C_4H_9$ | H | H | $OCH_3$ | H |
| t-$C_4H_9$ | H | H | $CH_3$ | 6-F |
| t-$C_4H_9$ | H | H | $CH_3$ | 6-$CH_3$ |
| t-$C_4H_9$ | H | H | Cl | 6-Cl |
| t-$C_4H_9$ | H | H | F | 6-$CH_3$ |
| t-$C_4H_9$ | 2-Cl | H | F | 6-F |
| t-$C_4H_9$ | 2-Br | H | F | 6-F |
| t-$C_4H_9$ | 2-$CH_3$ | H | F | 6-F |
| t-$C_4H_9$ | 2-$OC_2H_5$ | H | F | 6-F |
| t-$C_4H_9$ | 2-i-$C_3H_7$ | H | F | 6-F |
| t-$C_4H_9$ | 2,3-$(CH_3)_2$ | H | F | 6-F |
| t-$C_4H_9$ | 3-$CH_3$ | H | F | 6-F |
| H | 3-$SCH_3$ | H | F | 6-F |
| H | 3-S-n-$C_3H_7$ | H | F | 6-F |
| t-$C_4H_9$ | 2,6-$(CH_3)_2$ | H | F | 6-F |
| t-$C_4H_9$ | 2,6-$(CH_3)_2$ | H | Cl | 6-F |
| t-$C_4H_9$ | 2,3-$(CH_3)_2$ | H | Cl | 6-F |
| $CH_2CH_2OC_2H_5$ | H | H | F | 6-F |
| $CH_2CH_2OC_2H_5$ | 2-$CH_3$ | H | F | 6-F |
| $CH_2CH_2OC_2H_5$ | 2,6-$(CH_3)_2$ | H | F | 6-F |
| $CH_2CH_2OC_2H_5$ | 2,6-$Cl_2$ | H | F | 6-F |
| $CH_2CH_2OC_2H_5$ | 2-$CH_3$ | H | Cl | 6-F |
| t-$C_4H_9$ | H | $CH_3$ | F | 6-F |
| n-$C_8H_{17}$ | H | H | F | 6-F |
| n-$C_6H_{13}$ | H | H | F | 6-F |
| n-$C_{12}H_{25}$ | H | H | Cl | 6-F |
| n-$C_{16}H_{33}$ | H | H | F | 6-F |
| $(CH_2)_4CH_2Cl$ | H | H | F | 6-F |
| $(CH_2)_5CH_2Cl$ | H | H | F | 6-Cl |
| $(CH_2)_7CH_2Cl$ | H | H | F | 6-F |
| $(CH_2)_{15}CH_2Cl$ | H | H | F | 6-Cl |
| $CH_2CH_2OCH_3$ | H | H | F | 6-F |
| $CH_2CH_2OCH(CH_3)_2$ | H | H | F | 6-F |
| $CH_2CH_2OCH_2CH(CH_3)_2$ | H | H | F | 6-F |
| $CH_2CH_2O$-n-$C_3H_7$ | H | H | Cl | H |
| $CH_2CH_2O$-n-$C_4H_9$ | H | H | F | 6-Cl |
| $CH_2CH_2O$-n-$C_6H_{13}$ | H | H | F | 6-F |
| $CH_2CH_2O$-n-$C_{14}H_{29}$ | H | H | F | 6-F |
| $OC_6H_5$ | H | H | F | 6-F |
| $OC_6H_5$ | H | H | Cl | 6-F |
| $OC_6H_5$ | 2-$CH_3$ | H | F | 6-F |
| $OC_6H_5$ | 2,3-$(CH_3)_2$ | H | F | 6-F |
| $OC_6H_4(4$-$CH_3)$ | H | H | F | 6-F |
| $OC_6H_4(4$-$C_2H_5)$ | H | H | F | 6-F |
| $OC_6H_4(4$-n-$C_3H_7)$ | H | H | F | 6-F |
| $OC_6H_4(4$-n-$C_8H_{17})$ | H | H | F | 6-F |
| $OC_6H_4(4$-n-$C_6H_{13})$ | H | H | F | 6-F |
| $OC_6H_4(4$-F$)$ | H | H | F | 6-F |
| $OC_6H_4(4$-Cl$)$ | H | H | F | 6-F |
| $OC_6H_3(3$-$CH_3,4$-Cl$)$ | H | H | F | 6-F |

TABLE 1-continued

[Structure: CH(R³)–O–C₆H₄(R¹)(R²)ₚ with oxazoline ring containing R⁴]

| R¹ | (R²)ₚ | R³ | R⁶ | R⁷ |
|---|---|---|---|---|
| OC₆H₃(4-CH₃,3-Cl) | H | H | F | 6-F |
| OC₆H₄(4-OC₂H₅) | H | H | F | 6-F |
| OC₆H₄(4-O-n-C₄H₉) | H | H | F | 6-F |
| OC₆H₄(4-O-n-C₈H₁₇) | H | H | F | 6-F |
| OC₆H₄(4-CF₃) | H | H | F | 6-F |
| OC₆H₄(4-CH₂CH₂Cl) | H | H | F | 6-F |
| OC₆H₄(4-(CH₂)₃CH₂Cl | H | H | F | 6-F |
| OC₆H₄(4-(CH₂₇CH₂Cl) | H | H | Cl | H |
| OC₆H₄(4-(CH₂)₂—O—CH₂CH₃) | H | H | F | 6-F |
| OC₆H₄(4-(CH₂)₂—O—(CH₂)₅CH₃) | H | H | F | 6-Cl |
| OC₆H₄(4-CH₂—O—CH₃) | H | H | Cl | H |
| OC₆H₄(4-SCH₃) | 3,5-Cl₂ | H | F | 6-F |
| OC₆H₄(4-SC₂H₅) | 3,5-Cl₂ | H | F | 6-F |
| OC₆H₄(3-SC₂H₅) | 3,5-Cl₂ | H | F | 6-F |
| OC₆H₄(4-i-C₃H₇) | 3,5-Cl₂ | H | F | 6-F |
| OC₆H₄(4-S-n-C₃H₇) | 3,5-Cl₂ | H | F | 6-F |
| OC₆H₃(2-Cl,4-SCH₃) | 3,5-Cl₂ | H | F | 6-F |
| OC₆H₃(3-CH₃,4-SCH₃) | 3,5-Cl₂ | H | F | 6-F |
| OC₆H₄(4-SCF₂H) | 3,5-Cl₂ | H | F | 6-F |
| OC₆H₄(4-SCF₂CF₂H) | 3,5-Cl₂ | H | F | 6-F |
| OC₆H₄(4-CF₃) | 3,5-Cl₂ | H | F | 6-F |
| OC₆H₃(2-Cl,4-CF₃) | 3,5-Cl₂ | H | F | 6-F |
| OC₆H₃(2-CH₃,4-CF₃) | 3,5-Cl₂ | H | F | 6-F |
| OC₆H₂(2,6-Cl₂,4-CF₃) | 3,5-Cl₂ | H | F | 6-F |
| OC₆H₂(2,6-(CH₃)₂,4-CF₃) | 3,5-Cl₂ | H | F | 6-F |
| OC₆H₃(2-OCH₃,4-CF₃) | 3,5-Cl₂ | H | F | 6-F |
| OC₆H₃(2-Cl,4-OCH₃) | 3,5-Cl₂ | H | F | 6-F |
| OC₆H₃(2-CH₃,4-OCH₃) | 3,5-Cl₂ | H | F | 6-F |
| OC₆H₃(2-Cl,4-OCH₂CH₃) | 3,5-Cl₂ | H | F | 6-F |
| OC₆H₂(2,6-Cl₂,4-OCH₃) | 3,5-Cl₂ | H | F | 6-F |
| OC₆H₂(2,6-(CH₃)₂,4-OCH₃) | 3,5-Cl₂ | H | F | 6-F |
| OC₆H₄(4-CF₃) | 3,5-Cl₂ | H | Cl | 6-F |
| OC₆H₄(4-OCF₃) | 3,5-Cl₂ | H | Cl | 6-F |
| OC₆H₃(2-Cl,4-CF₃) | 3,5-Cl₂ | H | Cl | 6-F |
| OC₆H₂(2,6-Cl₂,4-CF₃) | 3,5-Cl₂ | H | Cl | 6-F |
| OC₆H₃(2-CH₃,4-CF₃) | 3,5-Cl₂ | H | Cl | 6-F |
| OC₆H₃(2-Cl,4-OCH₃) | 3,5-Cl₂ | H | Cl | 6-F |
| OC₆H₄(4-OCF₃) | 3-Cl | H | F | 6-F |
| OC₆H₄(4-OCF₂CF₂H) | 3-Cl | H | F | 6-F |
| OC₆H₄(4-OCF₂CClFH) | 3-Cl | H | F | 6-F |
| OC₆H₄(4-OCF₂CFHCF₃) | 3-Cl | H | F | 6-F |
| OC₆H₄(4-OCH₂CF₃) | 3-Cl | H | F | 6-F |
| OC₆H₄(4-SCH₃) | 3-Cl | H | F | 6-F |
| OC₆H₄(4-SC₂H₅) | 3-Cl | H | F | 6-F |
| OC₆H₄(3-SC₂H₅) | 3-Cl | H | F | 6-F |
| OC₆H₄(4-i-C₃H₇) | 3-Cl | H | F | 6-F |
| OC₆H₄(4-S-n-C₃H₇) | 3-Cl | H | F | 6-F |
| OC₆H₃(2-Cl,4-SCH₃) | 3-Cl | H | F | 6-F |
| OC₆H₃(3-CH₃,4-SCH₃) | 3-Cl | H | F | 6-F |
| OC₆H₄(4-SCF₂H) | 3-Cl | H | F | 6-F |
| OC₆H₄(4-SCF₂CF₂H) | 3-Cl | H | F | 6-F |
| OC₆H₄(4-CF₃) | 3-Cl | H | F | 6-F |
| OC₆H₃(2-Cl,4-CF₃) | 3-Cl | H | F | 6-F |
| OC₆H₃(2-CH₃,4-CF₃) | 3-Cl | H | F | 6-F |
| OC₆H₂(2,6-Cl₂,4-CF₃) | 3-Cl | H | F | 6-F |
| OC₆H₂(2,6-(CH₃)₂,4-CF₃) | 3-Cl | H | F | 6-F |
| OC₆H₃(2-OCH₃,4-CF₃) | 3-Cl | H | F | 6-F |
| OC₆H₃(2-Cl,4-OCH₃) | 3-Cl | H | F | 6-F |
| OC₆H₃(2-CH₃,4-OCH₃) | 3-Cl | H | F | 6-F |
| OC₆H₃(2-Cl,4-OCH₂CH₃) | 3-Cl | H | F | 6-F |
| OC₆H₂(2,6-Cl₂,4-OCH₃) | 3-Cl | H | F | 6-F |
| OC₆H₂(2,6-(CH₃)₂,4-OCH₃) | 3-Cl | H | F | 6-F |
| OC₆H₄(4-CF₃) | 3-Cl | H | Cl | 6-F |
| OC₆H₄(4-OCF₃) | 3-Cl | H | Cl | 6-F |
| OC₆H₃(2-Cl,4-CF₃) | 3-Cl | H | Cl | 6-F |
| OC₆H₂(2,6-Cl₂,4-CF₃) | 3-Cl | H | Cl | 6-F |
| OC₆H₃(2-CH₃,4-CF₃) | 3-Cl | H | Cl | 6-F |
| OC₆H₃(2-Cl,4-OCH₃) | 3-Cl | H | Cl | 6-F |
| C₆H₄(4-n-C₈H₁₇) | H | H | F | 6-F |

TABLE 1-continued

| R¹ | (R²)ₚ | R³ | R⁴ R⁶ | R⁴ R⁷ |
|---|---|---|---|---|
| C₆H₄(4-OC₂H₅) | H | H | F | 6-F |
| C₆H₄(4-Cl) | H | H | F | 6-F |
| C₆H₃(2,4-Cl₂) | H | H | F | 6-F |
| C₆H₃(2-Cl,4-CF₃) | H | H | F | 6-F |
| C₆H₄(4-n-C₅H₁₁) | H | H | F | 6-F |
| OC₆H₄(4-OCF₃) | 3,5-Cl₂ | H | F | 6-F |
| OC₆H₄(4-OCF₂CF₂H) | 3,5-Cl₂ | H | F | 6-F |
| OC₆H₄(4-OCF₂CClFH) | 3,5-Cl₂ | H | F | 6-F |
| OC₆H₄(4-OCF₂CFHCF₃) | 3,5-Cl₂ | H | F | 6-F |
| OC₆H₄(4-OCH₂CF₃) | 3,5-Cl₂ | H | F | 6-F |
| C₆H₄(4-Br) | H | H | F | 6-F |
| C₆H₄(4-n-C₄H₉) | H | H | F | 6-F |
| C₆H₄(4-i-C₄H₉) | H | H | F | 6-F |
| C₆H₃(3-Cl,4-CH₃) | H | H | F | 6-F |
| C₆H₄(4-sec-C₄H₉) | H | H | F | 6-F |
| C₆H₄(4-OCF₃) | H | H | F | 6-F |
| C₆H₃(2-Cl,4-n-C₃H₇) | H | H | F | 6-F |
| C₆H₄(4-Cl) | 2-Cl | H | F | 6-F |
| C₆H₄(4-n-C₃H₇) | 2-Cl | H | F | 6-F |
| C₆H₄(4-Cl) | 2-OCH₃ | H | F | 6-F |
| C₆H₃(3,5-Cl₂) | 2-OCH₃ | H | F | 6-F |
| C₆H₃(3,5-Cl₂) | 3-CH₃ | H | F | 6-F |
| C₆H₃(2,4-Cl₂) | 2-F | H | F | 6-F |
| C₆H₄(4-i-C₄H₉) | 3,5-(CH₃)₂ | H | F | 6-F |
| C₆H₃(3-Cl,4-CH₃) | 3,5-(CH₃)₂ | H | F | 6-F |
| C₆H₄(4-sec-C₄H₉) | 3,5-(CH₃)₂ | H | F | 6-F |
| C₆H₄(4-OCF₃) | 3,5-(CH₃)₂ | H | F | 6-F |
| C₆H₃(2-Cl,4-n-C₃H₇) | 3,5-(CH₃)₂ | H | F | 6-F |
| C₆H₂(2,6-Cl₂,4-CF₃) | 3,5-(CH₃)₂ | H | F | 6-F |
| C₆H₂(2,6-(CH₃)₂,4-CF₃) | 3,5-(CH₃)₂ | H | F | 6-F |
| C₆H₃(3,5-Cl₂) | 3,5-(CH₃)₂ | H | F | 6-F |
| C₆H₃(2-CH₃,4-CF₃) | 3,5-(CH₃)₂ | H | F | 6-F |
| C₆H₃(2-OCH₃,4-CF₃) | 3,5-(CH₃)₂ | H | F | 6-F |
| C₆H₃(2-OCH₂CH₃,4-CF₃) | 3,5-(CH₃)₂ | H | F | 6-F |
| C₆H₃(2,6-(OCH₃)₂,4-CF₃) | 3,5-(CH₃)₂ | H | F | 6-F |
| C₆H₃(2,6-(OCH₃)₂,4-Cl) | 3,5-(CH₃)₂ | H | F | 6-F |
| C₆H₃(2,3-Cl₂) | 3,5-(CH₃)₂ | H | F | 6-F |
| C₆H₂(2,3,4-Cl₃) | 3,5-(CH₃)₂ | H | F | 6-F |
| C₆H₂(2,3-Cl₂,4-CF₃) | 3,5-(CH₃)₂ | H | F | 6-F |
| C₆H₃(2-CF₃,4-Cl) | 3,5-(CH₃)₂ | H | F | 6-F |
| C₆H₄(4-CF₃) | 3,5-(CH₃)₂ | H | F | 6-F |
| C₆H₃(2-Cl,4-CF₃) | 3,5-(CH₃)₂ | H | Cl | 6-F |
| C₆H₃(2-CH₃,4-CF₃) | 3,5-(CH₃)₂ | H | Cl | 6-F |
| C₆H₂(2,6-Cl₂,4-CF₃) | 3,5-(CH₃)₂ | H | Cl | 6-F |
| C₆H₂(2,6-(CH₃)₂,4-CF₃) | 3,5-(CH₃)₂ | H | Cl | 6-F |
| C₆H₂(2-CH₃,6-Cl,4-CF₃) | 3,5-(CH₃)₂ | H | F | 6-F |
| C₆H₄(4-OC₂H₅) | 3-CH₃ | H | F | 6-F |
| C₆H₄(4-Cl) | 3-CH₃ | H | F | 6-F |
| C₆H₃(2,4-Cl₂) | 3-CH₃ | H | F | 6-F |
| C₆H₃(2-Cl,4-CF₃) | 3-CH₃ | H | F | 6-F |
| C₆H₄(4-n-C₅H₁₁) | 3-CH₃ | H | F | 6-F |
| C₆H₄(4-n-C₈H₁₇) | 3-CH₃ | H | F | 6-F |
| C₆H₄(4-Br) | 3-CH₃ | H | F | 6-F |
| C₆H₄(4-n-C₄H₉) | 3-CH₃ | H | F | 6-F |
| C₆H₄(4-i-C₄H₉) | 3-CH₃ | H | F | 6-F |
| C₆H₃(3-Cl,4-CH₃) | 3-CH₃ | H | F | 6-F |
| C₆H₄(4-sec-C₄H₉) | 3-CH₃ | H | F | 6-F |
| C₆H₄(4-OCF₃) | 3-CH₃ | H | F | 6-F |
| C₆H₃(2-Cl,4-n-C₃H₇) | 3-CH₃ | H | F | 6-F |
| C₆H₂(2,6-Cl₂,4-CF₃) | 3-CH₃ | H | F | 6-F |
| C₆H₂(2,6-(CH₃)₂,4-CF₃) | 3-CH₃ | H | F | 6-F |
| C₆H₃(3,5-Cl₂) | 3-CH₃ | H | F | 6-F |
| C₆H₃(2-CH₃,4-CF₃) | 3-CH₃ | H | F | 6-F |
| C₆H₃(2-OCH₃,4-CF₃) | 3-CH₃ | H | F | 6-F |
| C₆H₃(2-OCH₂CH₃,4-CF₃) | 3-CH₃ | H | F | 6-F |
| C₆H₃(2,6-(OCH₃)₂,4-CF₃) | 3-CH₃ | H | F | 6-F |
| C₆H₃(2,6-(OCH₃)₂,4-Cl) | 3-CH₃ | H | F | 6-F |
| C₆H₃(2,3-Cl₂) | 3-CH₃ | H | F | 6-F |
| C₆H₂(2,3,4-Cl₃) | 3-CH₃ | H | F | 6-F |

TABLE 1-continued

| $R^1$ | $(R^2)_p$ | $R^3$ | $R^4$ $R^6$ | $R^7$ |
|---|---|---|---|---|
| $C_6H_2(2,3-Cl_2,4-CF_3)$ | 3-$CH_3$ | H | F | 6-F |
| $C_6H_3(2-CF_3,4-Cl)$ | 3-$CH_3$ | H | F | 6-F |
| $C_6H_4(4-CF_3)$ | 3-$CH_3$ | H | F | 6-F |
| $C_6H_3(2-Cl,4-CF_3)$ | 3-$CH_3$ | H | Cl | 6-F |
| $C_6H_3(2-CH_3,4-CF_3)$ | 3-$CH_3$ | H | Cl | 6-F |
| $C_6H_2(2,6-Cl_2,4-CF_3)$ | 3-$CH_3$ | H | Cl | 6-F |
| $C_6H_2(2,6-(CH_3)_2,4-CF_3)$ | 3-$CH_3$ | H | Cl | 6-F |
| $C_6H_2(2-CH_3,6-Cl,4-CF_3)$ | 3-$CH_3$ | H | F | 6-F |
| $C_6H_4(4-OC_2H_5)$ | 3-Cl | H | F | 6-F |
| $C_6H_4(4-Cl)$ | 3-Cl | H | F | 6-F |
| $C_6H_3(2,4-Cl_2)$ | 3-Cl | H | F | 6-F |
| $C_6H_3(2-Cl,4-CF_3)$ | 3-Cl | H | F | 6-F |
| $C_6H_4(4-n-C_5H_{11})$ | 3-Cl | H | F | 6-F |
| $C_6H_4(4-n-C_8H_{17})$ | 3-Cl | H | F | 6-F |
| $C_6H_4(4-Br)$ | 3-Cl | H | F | 6-F |
| $C_6H_4(4-n-C_4H_9)$ | 3-Cl | H | F | 6-F |
| $C_6H_4(4-i-C_4H_9)$ | 3-Cl | H | F | 6-F |
| $C_6H_3(3-Cl,4-CH_3)$ | 3-Cl | H | F | 6-F |
| $C_6H_4(4-sec-C_4H_9)$ | 3-Cl | H | F | 6-F |
| $C_6H_4(4-OCF_3)$ | 3-Cl | H | F | 6-F |
| $C_6H_3(2-Cl,4-n-C_3H_7)$ | 3-Cl | H | F | 6-F |
| $C_6H_2(2,6-Cl_2,4-CF_3)$ | 3-Cl | H | F | 6-F |
| $C_6H_2(2,6-(CH_3)_2,4-CF_3)$ | 3-Cl | H | F | 6-F |
| $C_6H_3(3,5-Cl_2)$ | 3-Cl | H | F | 6-F |
| $C_6H_3(2-CH_3,4-CF_3)$ | 3-Cl | H | F | 6-F |
| $C_6H_3(2-OCH_3,4-CF_3)$ | 3-Cl | H | F | 6-F |
| $C_6H_3(2-OCH_2CH_3,4-CF_3)$ | 3-Cl | H | F | 6-F |
| $C_6H_3(2,6-(OCH_3)_2,4-CF_3)$ | 3-Cl | H | F | 6-F |
| $C_6H_3(2,6-(OCH_3)_2,4-Cl)$ | 3-Cl | H | F | 6-F |
| $C_6H_3(2,3-Cl_2)$ | 3-Cl | H | F | 6-F |
| $C_6H_2(2,3,4-Cl_3)$ | 3-Cl | H | F | 6-F |
| $C_6H_2(2,3-Cl_2,4-CF_3)$ | 3-Cl | H | F | 6-F |
| $C_6H_3(2-CF_3,4-Cl)$ | 3-Cl | H | F | 6-F |
| $C_6H_4(4-CF_3)$ | 3-Cl | H | F | 6-F |
| $C_6H_3(2-Cl,4-CF_3)$ | 3-Cl | H | Cl | 6-F |
| $C_6H_3(2-CH_3,4-CF_3)$ | 3-Cl | H | Cl | 6-F |
| $C_6H_2(2,6-Cl_2,4-CF_3)$ | 3-Cl | H | Cl | 6-F |
| $C_6H_2(2,6-(CH_3)_2,4-CF_3)$ | 3-Cl | H | Cl | 6-F |
| $C_6H_2(2-CH_3,6-Cl,4-CF_3)$ | 3-Cl | H | Cl | 6-F |
| $CH_2C_6H_5$ | H | H | F | 6-Cl |
| $CH_2C_6H_5$ | 2-$CH_3$ | H | F | 6-F |
| $CH_2C_6H_5$ | 2,3-$(CH_3)_2$ | H | F | 6-F |
| $CH_2C_6H_4(4-i-C_3H_7)$ | H | H | F | 6-F |
| $CH_2C_6H_4(4-t-C_4H_9)$ | H | H | F | 6-F |
| $CH_2C_6H_4(4-OC_2H_5)$ | H | H | F | 6-F |
| $CH_2C_6H_4(4-F)$ | H | H | F | 6-F |
| $OC_6H_4(4-OCF_3)$ | H | H | F | 6-F |
| $OC_6H_4(4-OCF_2CF_2H)$ | H | H | F | 6-F |
| $OC_6H_4(4-OCF_2CClFH)$ | H | H | F | 6-F |
| $OC_6H_4(4-OCF_2CFHCF_3)$ | H | H | F | 6-F |
| $OC_6H_4(4-OCH_2CF_3)$ | H | H | F | 6-F |
| $OC_6H_4(4-O(CH_2)_4Cl)$ | H | H | F | 6-F |
| $OC_6H_4(4-O(CH_2)_8Cl)$ | H | H | F | 6-Cl |
| $OC_6H_4(4-SCH_3)$ | H | H | F | 6-F |
| $OC_6H_4(4-SC_2H_5)$ | H | H | F | 6-F |
| $OC_6H_4(4-S-(CH_2)_3CH_3)$ | H | H | F | 6-F |
| $OC_6H_4(4-S-(CH_2)_7CH_3)$ | H | H | Cl | H |
| $OC_6H_4(4-S-(CH_2)_4Cl)$ | H | H | F | 6-F |
| $OC_6H_4(4-S-(CH_2)_8Cl)$ | H | H | F | 6-F |
| $c-C_6H_{11}$ | H | H | F | 6-F |
| $c-C_6H_{11}$ | H | H | Cl | 6-F |
| $c-C_6H_{11}$ | H | H | Cl | H |
| $c-C_6H_{10}(4-t-C_4H_9)$ | H | H | F | 6-F |
| $c-C_6H_{10}(4-t-C_4H_9)$ | H | H | F | 6-Cl |
| $c-C_6H_{10}(2-Cl)$ | H | H | Cl | H |
| $CH_2C_6H_5$ | H | H | F | 6-F |
| $C_6H_4(4-OC_2H_5)$ | 3,5-$(CH_3)_2$ | H | F | 6-F |
| $C_6H_3(4-Cl)$ | 3,5-$(CH_3)_2$ | H | F | 6-F |
| $C_6H_3(2,4-Cl_2)$ | 3,5-$(CH_3)_2$ | H | F | 6-F |

TABLE 1-continued

|  |  |  | R⁴ | |
|---|---|---|---|---|
| R¹ | (R²)ₚ | R³ | R⁶ | R⁷ |
| C₆H₃(2-Cl,4-CF₃) | 3,5-(CH₃)₂ | H | F | 6-F |
| C₆H₄(4-n-C₅H₁₁) | 3,5-(CH₃)₂ | H | F | 6-F |
| C₆H₄(4-n-C₈H₁₇) | 3,5-(CH₃)₂ | H | F | 6-F |
| C₆H₄(4-Br) | 3,5-(CH₃)₂ | H | F | 6-F |
| C₆H₄(4-n-C₄H₉) | 3,5-(CH₃)₂ | H | F | 6-F |
| OC₆H₄(3-SC₂H₅) | H | H | F | 6-F |
| OC₆H₄(4-S-i-C₃H₇) | H | H | F | 6-F |
| OC₆H₄(4-S-n-C₃H₇) | H | H | F | 6-F |
| OC₆H₃(2-Cl,4-SCH₃) | H | H | F | 6-F |
| OC₆H₃(3-CH₃,4-SCH₃) | H | H | F | 6-F |
| OC₆H₄(4-SCF₂H) | H | H | F | 6-F |
| OC₆H₄(4-SCF₂CF₂H) | H | H | F | 6-F |
| OC₆H₄(4-OC₂H₅) | 2-CH₃ | H | F | 6-F |
| OC₆H₄(4-OCF₂CF₂H) | 2,3-(CH₃)₂ | H | F | 6-F |
| OC₆H₄(4-SCH₃) | 2,6-(CH₃)₂ | H | F | 6-F |
| C₆H₅ | H | H | F | 6-F |
| H | 3-n-C₃H₇ | H | F | 6-F |
| H | 3-i-C₃H₇ | H | F | 6-F |
| H | 3-O-i-C₃H₇ | H | F | 6-F |
| n-C₁₀H₂₁ | H | H | F | 6-F |
| n-C₈H₁₇ | 2-F | H | F | 6-F |
| n-C₈H₁₇ | 2-Cl | H | F | 6-F |
| n-C₈H₁₇ | 2-CH₃ | H | F | 6-F |
| n-C₈H₁₇ | 2-OCH₃ | H | F | 6-F |
| n-C₉H₁₉ | 2-OCH₃ | H | F | 6-F |
| n-C₁₀H₂₁ | 2-CH₃ | H | F | 6-F |
| n-C₁₀H₂₁ | 2-Cl | H | F | 6-F |
| C₆H₄(4-CH₃) | H | H | F | 6-F |
| C₆H₄(4-OCH₃) | H | H | F | 6-F |
| C₆H₄(4-C₂H₅) | H | H | F | 6-F |
| CH₂C₆H₄(4-Cl) | H | H | F | 6-F |
| CH₂C₆H₄(4-Cl) | H | H | F | 6-Cl |
| CH₂C₆H₃(2,4-Cl₂) | H | H | F | 6-F |
| CH₂C₆H₄(3-Cl) | H | H | F | 6-F |
| CH₂C₆H₃(3,4-Cl₂) | H | H | F | 6-F |
| CH₂C₆H₄(4-n-C₈H₁₇) | H | H | F | 6-F |
| CH₂C₆H₃(2,4-F₂) | H | H | F | 6-F |
| Cl | H | H | H | 4-C₂H₅ |
| F | H | H | H | 4-i-C₃H₇ |
| F | H | H | H | 4-n-C₃H₇ |
| Cl | H | H | H | 4-OCH₃ |
| Cl | H | H | H | 4-OC₂H₅ |
| F | H | H | H | 4-O-n-C₃H₇ |
| Cl | H | H | H | 4-OCF₃ |
| H | H | H | H | 4-OCF₂CF₂H |
| H | H | H | H | 4-OCF₂CFHCF₃ |
| t-C₄H₉ | H | H | O-i-C₃H₇ | H |
| t-C₄H₉ | H | H | OC₂H₅ | H |
| i-C₃H₇ | H | H | OCH₃ | H |
| OC₆H₅ | 2-OC₂H₅ | H | F | 6-F |
| OC₆H₄(4-Cl) | 2-OC₂H₅ | H | F | 6-F |
| OC₆H₄(4-SCH₃) | 2-OC₂H₅ | H | F | 6-F |
| CF₃ | H | H | F | 6-F |
| OCF₃ | H | H | F | 6-F |
| OCF₂CF₂H | H | H | F | 6-F |
| OCH₂CF₃ | H | H | F | 6-F |
| OCF₂CFHCH₃ | H | H | F | 6-F |
| O(CH₂)₄CH₂Cl | H | H | F | 6-Cl |
| O(CH₂)₅CH₂Cl | H | H | F | 6-F |
| O(CH₂)₇CH₂Cl | H | H | F | 6-F |
| O(CH₂)₁₅CH₂Cl | H | H | Cl | H |
| SCF₃ | H | H | F | 6-F |
| SCF₂CF₂H | H | H | F | 6-F |
| SCF₂CFHCH₃ | H | H | F | 6-F |
| O-n-C₆H₁₃ | H | H | F | 6-F |
| O-n-C₈H₁₇ | H | H | F | 6-F |
| OCH₃ | H | H | F | 6-F |
| OC₂H₅ | H | H | F | 6-F |
| O-n-C₃H₇ | H | H | F | 6-F |

TABLE 1-continued

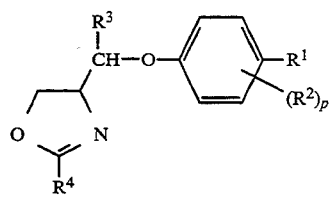

| $R^1$ | $(R^2)_p$ | $R^3$ | $R^4$ $R^6$ | $R^7$ |
|---|---|---|---|---|
| O-i-$C_3H_7$ | H | H | F | 6-F |
| O-n-$C_{10}H_{21}$ | H | H | F | 6-F |
| O-n-$C_{16}H_{33}$ | H | H | F | 6-F |
| O-n-$C_{12}H_{25}$ | H | H | F | 6-F |
| $SCH_3$ | H | H | F | 6-F |
| $SC_2H_5$ | H | H | F | 6-F |
| S-n-$C_3H_7$ | H | H | F | 6-F |
| S-n-$C_4H_9$ | H | H | F | 6-F |
| S-n-$C_5H_{11}$ | H | H | F | 6-F |
| S-n-$C_6H_{13}$ | H | H | F | 6-Cl |
| S-n-$C_8H_{17}$ | H | H | F | 6-F |
| S-n-$C_{10}H_{21}$ | H | H | F | 6-F |
| S-n-$C_{16}H_{33}$ | H | H | F | 6-F |
| $S(CH_2)_4CH_2Cl$ | H | H | F | 6-F |
| $S(CH_2)_5CH_2Cl$ | H | H | F | 6-Cl |
| $S(CH_2)_7CH_2Cl$ | H | H | F | 6-F |
| $S(CH_2)_{15}CH_2Cl$ | H | H | F | 6-Cl |
| $CH_2CH_2O$-n-$C_4H_9$ | H | H | F | 6-F |
| $CH_2CH_2O$-n-$C_6H_{13}$ | H | H | F | 6-F |
| $CH_2CH_2O$-n-$C_{10}H_{21}$ | H | H | F | 6-F |
| $CH_2CH_2O$-n-$C_3H_7$ | H | H | F | 6-F |
| c-$C_3H_5$ | H | H | F | 6-F |
| c-$C_3H_4$(1-$CH_3$) | H | H | F | 6-F |
| O-c-$C_6H_{11}$ | H | H | F | 6-F |
| O-c-$C_6H_{10}$(4-$CH_3$) | H | H | F | 6-F |
| O-c-$C_6H_{10}$(4-t-$C_4H_9$) | H | H | F | 6-F |
| O-c-$C_6H_{10}$(2-Cl) | H | H | F | 6-F |
| $SC_6H_5$ | H | H | F | 6-F |
| $SC_6H_4$(4-Cl) | H | H | F | 6-F |
| $SC_6H_4$(4-$CF_3$) | H | H | F | 6-F |
| $SC_6H_4$(4-$SCH_3$) | H | H | F | 6-F |
| $OC_6H(2,3,5,6-(CH_3)_4)$ | H | H | F | 6-F |
| O-n-$C_4H_9$ | 3,4,5,6-$F_4$ | H | F | 6-F |
| O-n-$C_4H_9$ | 3,4,5,6-$F_4$ | H | F | 6-Cl |
| t-$C_4H_9$ | H | H | $(CH_2)_2Cl$ | H |
| t-$C_4H_9$ | H | H | $(CH_2)_3Cl$ | H |
| $OCH_2C_6H_4$(4-Cl) | H | H | F | 6-F |
| $OCH_2C_6H_4$(4-n-$C_4H_9$) | H | H | Cl | H |
| $OCH_2C_6H_3$(2,6-$Cl_2$) | H | H | F | Cl |
| $OCH_2C_6H_4$(4-t-$C_4H_9$) | H | H | Cl | H |
| $OCH_2C_6H_4$(4-$CF_3$) | H | H | F | Cl |
| $OCH_2C_6H_3$(2-Cl,4-$CF_3$) | H | H | F | 6-F |
| $OCH_2C_6H_4$(4-$OCF_3$) | H | H | F | Cl |
| $OCH_2C_6H_3$(2-Cl,4-$OCF_3$) | H | H | F | 6-F |
| $OCH_2C_6H_2$(2,6-$Cl_2$,4-$CF_3$) | H | H | F | 6-F |
| $OCH_2C_6H_2$(2,6-$Cl_2$,4-$OCF_3$) | H | H | F | 6-F |

(c-$C_3H_5$: cyclopropyl)

Examples of harmful insects, mites and/or ticks against which the oxazoline derivatives (I) exhibit controlling effects are shown below.

Harmful insects belonging to Hemiptera:

Planthoppers such as small brown planthopper (*Laodelphax striatellus*), brown planthopper (*Nilaparvata lugens*), white-backed rice planthopper (*Sogatella furcifera*), etc.; leafhoppers such as green rice leafhopper (*Nephotettix cinticeps*), (*Nephotettix virescens*), etc.; aphids, bugs, whiteflies, scales, lace bugs, psyllids, etc.

Harmful insects belonging to Lepidoptera:

Pyralidae such as rice stem borer (*Chilo suppressalis*), rice leafroller (*Cnaphalocrocis medinalis*), european corn borer (*Ostrinia nubilalis*), bluegrass webworm (*Parapediasia teterrella*), cotton leafroller (*Notarcha derogata*), indian meal moth (*Plodia interpunctella*), etc.; Noctuidae such as tobacco cutworm (*Spodoptera litura*), rice armyworm (*Pseudaletia separata*), cabbage armyworm (*Mamestra brassicae*), black cutworm (*Agrotis ipsilon*), cabbage looper (*Trichoplusia ni*), Heliothis spp., Helicoverpa spp., etc.; Pieridae such as common cabbage worm (*Pieris rapae crucivora*), etc.; Tortricidae such as Adoxophyes spp. oriental fruit moth (*Grapholita molesta*), codling moth (*Cydia pomonella*), etc.; Carposinidae such as peach fruit moth (*Carposina niponensis*), etc.; Lyonetiidae such as Lyonetia spp., etc.; Lymantriidae such as Lymantria spp., Euproctis spp., etc.; Yponomeutidae such as diamondback moth (*Plutella xylostella*), etc.; Gelechiidae such as pink bollworm (*Pectinophora gossypiella*), etc.; Arctiidae such as fall webworm (*Hyphantria cunea*), etc.; Tineidae such as casemaking clothes moth (*Tinea translucens*), webbing clothes moth (*Tineola bisselliella*), etc.; etc.

Harmful insects belonging to Diptera:

Mosquitos such as common mosquito (*Culex pipiens pallens*), *Culex tritaeniorhynchus*, etc.; *Aedes* spp. such as *Aedes aegypti*, *Aedes albopictus*, etc.; *Anopheles* spp. such as *Anopheles sinensis*, etc.; midges (Chironmoidae); Muscidae such as housefly (*Musca domestica*), false stablefly (*Muscina stabulans*), etc.; Calliphoridae; Sarcophagidae; lesser housefly (*Fannia canicularis*); Anthomyiidae or anthomyiid flies such as seedcorn maggot (*Delia platura*), onion maggot (*Delia antiqua*), etc.; fruit flies (Tephritidae); small fruit flies (Drosophilidae); moth flies (Psychodidae); black flies (Simuliidae); Tabanidae; stable flies (Stomoxyidae); leafminer flies (Agromyzidae); etc.

Harmful insects belonging to Coleoptera:

Corn rootworms such as western corn rootworm (*Diabrotica virgifera*), southern corn rootworm (*Diabrotica undecimpunctata*), etc.; scarabs (Scarabaeidae) such as cupreous chafer (*Anomala cuprea*), soybeen beetle (*Anomala rufocuprea*), etc.; weevils such as maize weevil (*Sitophilus zeamais*), rice water weevil (*Lissorhoptrus oryzophilus*), alfalfa weevil (*Hypera pastica*), adzuki been weevil (*Calosobruchys chinensis*), etc.; darkling beetles (Tenebrionidae), such as yellow mealworm (*Tenebrio molitor*), red fluor beetle (*Tribolium castaneum*), etc.; leaf beetles (Chrysomelidae) such as cucurbit leaf beetle (*Aulacophora femoralis*), striped flea beetles (*Phyllotreta striolata*), Colorado potate beetle (*Leptinotarsa decemlineata*), etc.; Anobiidae; Epilachna spp. such as twenty-eight-spotted ladybirds (*Epilachna vigintioctopunctata*), etc.; powderpost beetles (Lyctidae), false powderpost beetles (Bostrychidae), Cerambycidae; robe beetle (*Paederus fuscipes*), etc.

Harmful insects belonging to Dictyoptera:

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), etc.

Harmful insects belonging to Thysanoptera:

*Thrips palmi*, *Thrips tabaci*, flower thrips (*Thrips hawaiiensis*), etc.

Harmful insects belonging to Hymenoptera:

ants (Formicidae); hornets (Vespidae); bethylid wasps (Bethylidae); sawflies (Tenthredinidae) such as cabbage sawfly (*Athalia rosae ruficornis*), etc.

Harmful insects belonging to Orthoptera:

mole crickets (Gryllotalpidae); grasshoppers (Acrididae), etc.

Harmful insects belonging to Aphaniptera:

*Purex irritans*, etc.

Harmful insects belonging to Anoplura:

*Pediculus humanus capitis*, *Phthirus pubis*, etc.

Harmful insects belonging to Isoptera:

*Reticulitermes speratus*, Formosan subterranean termite (*Coptotermes formosanus*), etc.

Harmful mites and ticks belonging to Acarina:

Tetranychidae such as two-spotted spider mite (*Tetranychus uriticae*), carmine spider mite (*Tetranychus cinnabarinus*), kanzawa spider mite (*Tetranychus kanzawai*), citrus red mite (*Panonychus citri*), european red mite (*Panonychus ulmi*), *Oligonychus* spp., etc.; Eriophyidae such as pink citrus rust mite (*Aculops pelekassi*), purple tea mite (*Calacarus carinatus*), etc.; Tarsonemidae such as broad mite (*Polyphagotarsonemus latus*), etc.; Tenuipalpidae; Tuckerellidae; Ixodidae such as *Boophilus microplus*, etc.; Housedust mites such as Acaridae, Pyroglyphidae, Cheyletidae, Dermanyssidae, etc.

Among the insect pests mites and/or ticks as above exemplified, the oxazoline derivatives (I) are particularly effective in controlling those belonging to Acarina and also exhibit a remarkable controlling effect on spider mites in an orchard or a field of vegetables or tea, etc.

The oxazoline derivatives (I) may be used alone as insecticides or in mixtures with other insecticides and/or acaricides to enhance or expand their insecticidal, acaricidal and/or pesticidal use.

Examples of the other insecticides and/or acaricides include organophosphorus compounds (e.g. fenitrothion (O,O-dimethyl O-(3-methyl-4-nitrophenyl) phosphorothioate), fenthion (O,O-dimethyl O-[3-methyl-4-(methylthio)phenyl]phosphorothioate), diazinon (O,O-diethyl-O-(2-isopropyl-6-methylpyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O,-ethyl O-4(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-dimethyl-S-(N-methylcarbamoylmethyl)dithiophosphate), phenthoate (ethyl 2-dimethoxyphosphinothioylthio(phenyl) acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphorodithioate), monocrotophos (dimethyl (E)-1-methyl-2-(methylcarbamoyl)vinyl phosphate), ethion (O,O,O',O'-tetraethyl S,S'-methylenebis (phosphorodithioate)), etc.; carbamate derivatives (e.g. BPMC (2-sec-butylphenyl methylcarbamate), benfuracarb (ethyl N-[2,3-dihydro-2,2-dimethylbenzofuran-7-yloxycarbonyl(methyl)aminothio]-N-isopropyl-β-alaninate), propoxur (2-isopropoxyphenyl N-methylcarbamate), carbosulfan (2,3-dihydro-2,2-dimethyl-7-benzofluranyl[(dibutylamino) thio]methyl carbamate), carbaryl (1-naphthyl-N-methylcarbamate), methomyl (S-methyl-N[(methylcarbamoyl)oxy]thioacetimidate), ethiofencarb [2-(ethylthiomethyl)phenyl methylcarbamate], aldicarb [2-methyl-2-(methylthio)propionaldehyde O-methylcarbamoyloxime], oxamyl (N,N-dimethyl-2-[methylcarbamoyloxyimino-2-(methylthio)acetamide), fenothiocarb ((S-4-phenoxybutyl)-N,N-dimethylthiocarbamate), etc.); pyrethroides (e.g. ethofenprox [2-(4-ethoxyphenyl)-2-methylpropyl-3-phenoxybenzyl ether], fenvalerate ((RS)-α-cyano-3-phenoxybenzyl (RS)-2-(4-chlorophenyl)-3-methylbutyrate), esfenvalerate [(S)-α-cyano-3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS,3RS)-(1RS,3RS)-3-(2,2-dichlorovinyl)-2,2dimethylcyclopropanecarboxylate]. permethrin (3-phenoxybenzyl (1RS,3RS)-(1RS,3RS)-3-(2,2-dichlorovinyl)-2,2-dimethylcyclopropanecarboxylate), cyhalothrin [(R,S)-α-cyano-3-phenoxybenzyl (Z)-(1RS,3RS)-3-(2-chloro-3,3,3-trifluoropropenyl)-2,2-dimethylcyclopropanecarboxylate), deltamethrin [(S)-α-cyano-m-phenoxybenzyl (1R,3R)-3-(2,2-dibromovinyl)- 2-dimethylcyclopropanecarboxylate], cycloprothrin [(RS)-α-cyano-3-phenoxybenzyl (RS)-2,2-dichloro-1-(4-ethoxyphenyl)-cyclopropanecarboxylate], fluvalinate (α-cyano-3-phenoxybenzyl N-(2-chloro-α,α,α-trifluoro-p-tolyl)-D-valinate), bifenthrin (2-methylbiphenyl-3-ylmethyl(Z)-(1RS)-cis-3-(2-chloro-3,3,3-trifluoroprop-1-enyl)-2,2-dimethylcyclopropanecarboxylate), acrinathrin ([1R-{1α(S*), 3-α(Z)}]-2,2-dimethyl-3-[3-oxo-3-(2,2,2-trifluoro-1-(trifluoromethyl)ethoxy-1-propenyl]cyclopropanecarboxylic acid, cyano(3-phenoxyphenyl)-methyl ester), 2-methyl-2-(4-bromodifluoromethoxyphenyl)propyl (3-phenoxybenzyl)ether, tralomethrin [(1R,3S)3[(1'RS)(1',2',2',2'-tetrabromoethyl)]-2,2-dimethylcyclopropane carboxylic acid (S)-α-cyano-3-phenoxybenzyl ester), silafluofen (4-ethoxyphenyl [3-(4-fluoro-3-phenoxyphenyl)propyl]dimethylsilane, etc.; thiadiazine derivatives (e.g. buprofezin (2-tert-butylimino-3-isopropyl-5-phenyl-1,3,5-triadiazin-4-one), etc.); nitroimidazolidine derivatives (e.g. imidacloprid [1-(6-chloro-3-pyridylmethyl)-N-nitroimidazolidin-2-ylideneamine], etc.); N-cyanoamidine (e.g. N-cyano-N'-methyl-N'-(6-chloro-3-pyridylmethyl) acetoamidine, etc.); nereistoxin derivatives (e.g. cartap [S,S'-(2-dimethylaminotrimethylene) bis(thiocarbamate), thiocyclam (N,N-dimethyl-1,2,3-trithian-5-ylamine), bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide), γ-BHC (1,2,3,4,5,6-hexachlorocyclohexane), 1,1-bis(chlorophenyl)-2,2,2-trichloroethanol, etc.); benzoylphenylurea derivatives (e.g. chlorfluazuron [1-(3,5-dichloro-4-(3-chloro-5-trifluoromethylpyridin-2-yloxy)phenyl]-3-(2,6-difluorobenzoyl-)urea), teflubenzuron [1-(3,5-dichloro-2,4-difluorophenyl)-3-(2,6-difluorobenzoyl)urea], flufenoxuron [1-[4-(2-chloro-4-trifluoromethylphenoxy)-2-fluorophenyl]-3-(2,6-difluorobenzoyl]urea, etc.); formamidine derivatives (e.g. amitraz [N,N'-[(methylimino)dimethylidyne]-di-2,4-xylidine], chlordimeform [N'-(4-chloro-2-methylphenyl)-N,N-dimethylmethanimidamide], diafenthiuron [N-(2,6-diisopropyl-4-phenoxyphenyl)-N'-tert-butylcarbodiimide], etc.); bromopropylate [isopropyl 4,4'-dibromobenzilate], tetradifon [4-chlorophenyl 2,4,5-trichlorophenylsulfone], quinomethionate [S,S-6-methylquinoxalin-2,3-diyldithiocarbonate], propargite [2-[4-(1,1-dimethylethyl)phenoxy]-cyclohexyl 2-propynyl sulfite], fenbutatin oxide [hexakis (2-methyl-2-phenylpropyl)distannoxane], hexythiazox [(4RS,5RS)-5-(4-chlorophenyl)-N-chlorohexyl-4-methyl-2-oxo-1,3-thiazolidine-3-carboxamide], clofentezine [3,6-bis(2-chlorophenyl)-1,2,4,5-tetrazine], pyridaben [2-tert-butyl-5-[4-tert-butylbenzylthio]-4-chloropyridazin-3(2H)-one], fenpyroximate [tert-butyl (E)-4-[(1,3)-dimethyl-5-phenoxypyrazole-4-yl)methylene aminooxymethyl]benzoate], tebufenpyrad [N-(4-tertbutylbenzyl)- 4-chloro-3-ethyl-l-methyl-5-pyrazole carboxamide], polynactins [tetranactin, dinactin, trinactin], milbemectin, avermectin, ivermectin, azadirachtin [AZAD], pyrimidifen [5-chloro-N-[2-{4-(2-ethoxyethyl)-2,3-dimethylphenoxy}ethyl]-6-ethylpyrimidin-4-amine, etc.

On the practical use of the oxazoline derivatives (I) as insecticides and/or acaricides, they may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosols, heating smoking formulations (e.g. self-burning-type smoking formulations, chemical reaction-type smoking formulations, porous ceramic plate-type smoking formulations), ULV formulations, poison baits, etc.

The composition of the present invention contains generally the oxazoline derivative(s) (I) as the active ingredient in an amount of from about 0.1% to 95% by weight based on the composition.

Examples of the solid carrier usable for making the composition are fine powders or granules of clays (e.g. kaolin clay, diatomaceous earth, synthetic hydrated silica, bentonite, Fubasami clay, terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyvinyl alcohol, polyvinyl-pyrrolidone, polyacrylic acid), etc. Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids, and esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reaction-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazines, dinitrosopentamethylenetetramine, polystyrene and polyurethane, fillers such as natural fiber pieces and synthetic fiber pieces, etc. The base material for poison baits may contain feed components such as crop powders, essential vegetable oils, sugars and crystalline cellulose, antioxidants such as dibutylhydroxytolune and nordihydroguaiaretic acid, preservatives such as dehydroacetic acid, feeding error preventing agents such as red paper powders, incentive flavors such as cheese flavor and onion flavor, etc.

Flowable concentrates (water-based suspension or emulsion formulations) are generally obtained by dispersing about 1 to 75 parts by weight of the oxazoline derivative (I) as the active ingredient finely and uniformly into water containing about 0.5 to 15 parts by weight of a dispersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anticorrosive agent, a stabilizing agent, a spreading agent, penetration auxiliaries, an antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc. Examples of the compounds giving a thixotropic property are bentonite, aluminum magnesium silicate, xanthane gum, polyacrylic acid, etc.

The compositions of the present invention thus obtained may be used as such or after diluting with water, etc. They may also be used in a mixture with any other active components or compositions chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active components or compositions.

For the purpose of controlling insects and/or mites in the agricultural field, the oxazoline derivative (I) according to the present invention may be applied to the insects and/or mites or the locus where the insects and/or mites propagate, generally in an amount of about 1 g to 500 g, and preferably about 10 g to 100 g per 10 ares. When the oxazoline derivative (I) is applied in a form of emulsifiable concentrate, wettable powder, flowable concentrate or the like after dilution with water, its concentration may be from about 0.1 to 1000 ppm. Granules, dusts, etc. may be used as such, i.e. without water dilution. When the oxazoline derivative (I) is used for household or public hygiene, it may be used in the form of emulsifiable concentrate, wettable powder, flowable concentrate or the like with water dilution, etc. In this case, the concentration of the active ingredient may be from about 0.01 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insects, mites and ticks, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

PRODUCTION EXAMPLE 1

(Production of Compound No. 1)

To a mixture of 1.46 g (6.54 mmol.) of 2-amino-3-[4-(1,1-dimethylethyl)phenoxy]propanol, 0.86 g (8.50 mmol.) of triethylamine and 20 ml of anhydrous tetrahydrofuran, there was added dropwise a solution of 1.15 g (6.54 mmol.) of 2,6-difluorobenzoylchloride in 10 ml of anhydrous tetrahydrofuran with stirring at a temperature of from 5° C. to 10° C. for 5 minutes. After addition, the reaction mixture was stirred at room temperature for one hour. After the reaction was completed, the resultant mixture was concentrated under reduced pressure. To the residue, there was added 20 ml of benzene and 10 ml of thionyl chloride and the reaction mixture was refluxed by heating with stirring for 3 hours. Then the reaction mixture was cooled to room temperature and concentrated under reduced pressure. To the residue, there was added 20 ml of ethanol and further added dropwise 1.4 ml of a 5N aqueous solution of sodium hydroxide with stirring at a temperature of 60° C. for 5 minutes. The reaction mixture was then stirred at the same temperature for 3 hours. After the reaction was completed, the reaction mixture was cooled to room temperature and concentrated under reduced pressure. To the residue, there was added 100 ml of ethyl acetate. The mixture was washed with water, dried over anhydrous magnesium sulfate and concentrated under reduced pressure. The residue was subjected to silica gel chromatography to give 1.72 g of 2-(2,6-difluorophenyl)-4-{[4-(1,1-dimethylethyl)phenoxy]methyl}-2-oxazoline as a colorless oily substance ($n_D^{19.1}$ 1.5391).

PRODUCTION EXAMPLE 2

(Production of Compounds Nos. 2, 49, 50 and 51)

Following the same procedure with the same molar proportion of materials as in Production Example 1, 2-(2,6-difluorophenyl)-4-{[2,3-dimethyl-4-(2-ethoxyethyl)phenoxy]methyl}-2-oxazoline (Compound No. 2) is obtained by using 2-amino-3-[2,3-dimethyl-4-(2ethoxyethyl)phenoxy]propanol instead of 2-amino-3-[4-(1,1-dimethylethyl)phenoxy]propanol. In the same way, 2-(2,6-difluorophenyl)-4-[(4-benzyl-2,3-dimethylphenoxy) methyl]-2-oxazoline (Compound No. 49), 2-(2,6-difluorophenyl)-4-{[4-(2-ethoxyethyl)-2-methylphenoxy]methyl}-2-oxazoline (Compound No. 50) or 2-(2,6-difluorophenyl)-4-{(4-benzyl-2-methylphenoxy)-methyl}-2-oxazoline (Compound No. 51) is obtained by using 2-amino-3-(4-benzyl-2,3-dimethylphenoxy)-propanol, 2-amino-3-[4-(2-ethoxyethyl)-2-methylphenoxy]propanol or 2-amino-3-[4-benzyl-2-methylphenoxy)propanol, respectively.

PRODUCTION EXAMPLE 3

(Production of Compounds Nos. 52 and 53)

Following the same procedure with the same molar proportion of materials as in Production Example 1, 2-(2-chloro-6-fluorophenyl)-4-{[4-(1,1-dimethylethyl)- phenoxy]methyl}-2-oxazoline (Compound No. 52) is obtained by using 2-chloro-6-fluorobenzoylchloride instead of 2,6-difluorobenzoylchloride. In the same way, 2-(2-chlorophenyl)-4-{[4-(1,1-dimethylethyl)phenoxy]methyl}-2-oxazoline (Compound No. 53) is obtained by using 2-chlorobenzoylchloride.

PRODUCTION EXAMPLE 4

(Production of Compound No. 36)

To a mixture of 1.14 g (4.40 mmol. ) of 2-amino-3-(4-phenoxyphenoxy)propanol, 0.58 g (5.72 mmol.) of triethylamine and 20 ml of anhydrous tetrahydrofuran, there was added dropwise a solution of 0.78 g (4.40 mmol.) of 2,6-difluorobenzoylchloride in 10 ml of anhydrous tetrahydrofuran with stirring at a temperature of from 5° C. to 10° C. for 5 minutes. After addition, the reaction mixture was stirred at room temperature for 2 hours. The above mixture was filtrated with a filter glass to remove the resultant precipitate and the filtrate was concentrated under reduced pressure. To the residue, there was added 20 ml of toluene and 10 ml of thionyl chloride and the reaction mixture was refluxed by heating with stirring for 5 hours. The reaction mixture was cooled;to room temperature and concentrated under reduced pressure. To the residue, there was added 20 ml of methanol and further added dropwise 1 ml of a 5N aqueous solution of sodium hydroxide with stirring at a temperature of 60° C. for 5 minutes. Then the reaction mixture was stirred at the same temperature for 5 hours. After the reaction was completed, the reaction mixture was cooled to room temperature and concentrated under reduced pressure. To the residue, there was added 100 ml of ethyl acetate. The mixture was washed with water, dried over anhydrous magnesium sulfate and concentrated under reduced pressure. The residue was subjected to silica gel chromatography to give 1.28 g of 2-(2,6-difluorophenyl)-4-[(4-phenoxyphenoxy)methyl]-2-oxazoline as a colorless oily substance ($n_D^{19.1}$ 1.5814).

PRODUCTION EXAMPLE 5

(Production of Compound No. 13)

To a mixture of 200 mg (0.938 mmol.) of 2-(2,6-difluorophenyl)-4-hydroxymethyl-2-oxazoline, 468 μl (1.87 mmol.) of tri-n-butylphosphine and 2 ml of anhydrous tetrahydrofuran, there was added dropwise a solution of 296 μl (1.88 mmol.) of diethylazodicarboxylate with stirring at a temperature of −25° C. for 5 minutes. Then the reaction mixture was allowed to warm to room temperature for 6 hours and then the above mixture was stirred at the same temperature. After the reaction was completed, the reaction mixture was concentrated under reduced pressure. The residue was subjected to silica gel chromatography to give 200 mg of 2-(2,6-difluorophenyl)-4-{[2,6-dimethyl-4-(4-chlorophenyl)phenoxy]methyl}-2-oxazoline as a colorless oily substance ($n_D^{23.5}$ 1.5552).

PRODUCTION EXAMPLE 6

(Production of Compound No. 17)

A mixture of 200 mg (0.687 mmol.) of 2-(2,6-difluorophenyl)-4-methanesulfonyloxymethyl-2-oxazoline, 232 mg (1.00 mmol.) of 4-(4-chlorophenyl)phenol, 24 mg (1.0 mmol.) of sodium hydroxide and 3 ml of N,N-dimethylformamide was stirred at room temperature for 24 hours. After the reaction was completed, the reaction mixture was poured into 50 ml of a 10% aqueous solution of ammonium chloride and extracted twice with ethyl acetate. The residue was dried over magnesium sulfate and concentrated under reduced pressure. The residue was subjected to silica gel chromatography to give 50 mg of 2-(2,6-difluorophenyl)-4-{[4-(4-chlorophenyl) phenoxy]methyl}-2-oxazoline as a white solid (m.g. 99.5° C.).

PRODUCTION EXAMPLE 7

(Production of Compounds Nos. 54, 55, 56, 57 and 58)

Following the same procedure with the same molar proportion of materials as in Production Example 5, 2-(2,6-difluorophenyl)-4-{[4-(4-methoxyphenoxy) phenoxy]methyl}-2-oxazoline (Compound No. 54) is obtained by using 4-(4-methoxyphenoxy)phenol instead of 4-(4-chloro-2,6-dimethylphenyl)phenol. In the same way, 2-(2,6-difluorophenyl)-4-{[4-(4-ethylphenoxy) phenoxy]methyl}-2-oxazoline (Compound No. 55), 2-(2,6-difluorophenyl)-4-{[4-(4-methoxyphenyl)phenoxy]methyl}-2-oxazoline (Compound No. 56), 2-(2,6-difluorophenyl)-4-[(4-benzylphenoxy)methyl]-2-oxazoline (Compound No. 57) or 2-(2,6-difluorophenyl)-4-{[2-methoxy-4-(4-chlorophenyl)phenoxy]methyl}-2-oxazoline (Compound No. 58) is obtained by using 4-(4-ethylphenoxy)phenol, 4-(4-methoxyphenyl)phenol, 4-benzylphenol or 2-methoxy-4-(4-chlorophenyl)phenol, respectively.

In the same manner as above, the following compounds are obtained.

| | |
|---|---|
| (1) 2-(2,6-difluorophenyl)-4-{[4-(1,1-dimethylethyl) phenoxy]methyl}-2-oxazoline | $n_D^{19.1}$ 1.5391 |
| (2) 2-(2,6-difluorophenyl)-4-{[2,3-dimethyl-4-(2-ethoxyethyl)phenoxy]methyl}-2-oxazoline | $n_D^{20.9}$ 1.5200 |
| (3) 2-(2,6-difluorophenyl)-4-{[2,6-dimethyl-4-(2-ethoxyethyl)phenoxy]methyl}-2-oxazoline | $n_D^{24.6}$ 1.4804 |
| (4) 2-(2,6-difluorophenyl)-4-[(4-cyclohexyl-phenoxy)methyl]-2-oxazoline | $n_D^{24.0}$ 1.5373 |
| (5) 2-(2,6-difluorophenyl)-4-[(4-cyclopentyl-phenoxy)methyl]-2-oxazoline | $n_D^{24.0}$ 1.5399 |
| (6) 2-(2,6-difluorophenyl)-4-[(4-n-heptyl-phenoxy)methyl]-2-oxazoline | $n_D^{24.0}$ 1.5215 |
| (7) 2-(2,6-difluorophenyl)-4-{[4-(1,1,2,2-tetrafluoro-ethylthio)phenoxy]methyl}-2-oxazoline | $n_D^{23.1}$ 1.5310 |
| (8) 2-(2,6-difluorophenyl)-4-{[3,5-dimethyl-4-[(4-ethylphenoxy)methyl]phenoxy]methyl}-2-oxazoline | |
| (9) 2-(2,6-difluorophenyl)-4-{[4-[(4-trifluoromethoxy-phenoxy)methyl]phenoxy]methyl}-2-oxazoline | |
| (10) 2-(2,6-difluorophenyl)-4-{[4-(4-bromophenyl) phenoxy]methyl}-2-oxazoline | m.p. 121.7° C. |
| (11) 2-(2,6-difluorophenyl)-4-{[2-chloro-4-(4- | $n_D^{23.4}$ 1.5780 |

-continued

| | |
|---|---|
| chlorophenyl)phenoxy]methyl}-2-oxazoline | |
| (12) 2-(2,6-difluorophenyl)-4-{[4-(3-chlorophenyl)phenoxy]methyl}-2-oxazoline | resinoid |
| (13) 2-(2,6-difluorophenyl)-4-{[3,5-dimethyl-4-(4-chlorophenyl)phenoxy]methyl}-2-oxazoline | $n_D^{23.5}$ 1.5552 |
| (14) 2-(2,6-difluorophenyl)-4-{[4-(4-ethylphenyl)phenoxy]methyl}-2-oxazoline | m.p. 92.0° C. |
| (15) 2-(2,6-difluorophenyl)-4-{[3,5-dimethyl-4-(4-ethylphenyl)phenoxy]methyl}-2-oxazoline | $n_D^{23.6}$ 1.5525 |
| (16) 2-(2,6-difluorophenyl)-4-{[4-(3-methylphenyl)phenoxy]methyl}-2-oxazoline | $n_D^{23.6}$ 1.5717 |
| (17) 2-(2,6-difluorophenyl)-4-{[ 4-(4-chlorophenyl)phenoxy]methyl}-2-oxazoline | m.p. 99.5° C. |
| (18) 2-(2,6-difluorophenyl)-4-{[2-chloro-4-(4-methylphenyl)phenoxy]methyl}-2-oxazoline | $n_D^{23.6}$ 1.5726 |
| (19) 2-(2,6-difluorophenyl)-4-{[4-(4-methylphenyl)phenoxy]methyl}-2-oxazoline | m.p. 88.1° C. |
| (20) 2-(2,6-difluorophenyl)-4-{[4-(3,4-dichlorophenyl)phenoxy]methyl}-2-oxazoline | resinoid |
| (21) 2-(2,6-difluorophenyl)-4-[(4-phenylphenoxy)methyl]-2-oxazoline | $n_D^{21.4}$ 1.5389 |
| (22) 2-(2,6-difluorophenyl)-4-[(2-chloro-4-phenylphenoxy)methyl]-2-oxazoline | resinoid |
| (23) 2-(2,6-difluorophenyl)-4-{[2-chloro-4-(3,4-dichlorophenyl)phenoxy]methyl}-2-oxazoline | m.p. 120.7° C. |
| (24) 2-(2,6-difluorophenyl)-4-{[2-chloro-3,5-dimethyl-4-(4-chlorophenyl)phenoxy]methyl}-2-oxazoline | $n_D^{22.4}$ 1.5748 |
| (25) 2-(2,6-difluorophenyl)-4-{[4-(4-chloro-2-methylphenyl)phenoxylmethyl}-2-oxazoline | $n_D^{23.1}$ 1.5765 |
| (26) 2-(2,6-difluorophenyl)-4-{[4-(3,5-dichlorophenyl)-phenoxy]methyl}-2-oxazoline | $n_D^{23.0}$ 1.5965 |
| (27) 2-(2,6-difluorophenyl)-4-{[4-(4-trifluoromethylphenyl)phenoxy]methyl}-2-oxazoline | m.p. 137.0° C. |
| (28) 2-(2,6-difluorophenyl)-4-{[4-(4-trifluoromethoxyphenyl)phenoxy]methyl}-2-oxazoline | m.p. 115.0° C. |
| (29) 2-(2,6-difluorophenyl)-4-{[2-chloro-4-(4-trifluoromethylphenyl)phenoxy]methyl}-2-oxazoline | m.p. 114.7° C. |
| (30) 2-(2,6-difluorophenyl)-4-{[2-chloro-4-(4-trifluoromethoxyphenyl)phenoxy]methyl}-2-oxazoline | m.p. 90.5° C. |
| (31) 2-(2,6-difluorophenyl)-4-[(4-benzyloxyphenoxy)methyl]-2-oxazoline | resinoid |
| (32) 2-(2,6-difluorophenyl)-4-{[4-(4-methylbenzyloxy)phenoxy]methyl}-2-oxazoline | m.p. 102.4° C. |
| (33) 2-(2,6-difluorophenyl)-4-{[4-(4-chlorobenzyloxy)phenoxy]methyl}-2-oxazoline | m.p. 114.8° C. |
| (34) 2-(2,6-difluorophenyl)-4-{[4-(2,4-dichlorobenzyloxy)phenoxy]methyl}-2-oxazoline | m.p. 118.8° C. |
| (35) 2-(2,6-difluorophenyl)-4-{[4-(4-methoxybenzyloxy)phenoxy]methyl}-2-oxazoline | m.p. 99.5° C. |
| (36) 2-(2,6-difluorophenyl)-4-[(4-phenoxyphenoxy)methyl]-2-oxazoline | $n_D^{19.1}$ 1.5814 |
| (37) 2-(2,6-difluorophenyl)-4-{[4-(4-methylthiophenoxy)phenoxy]methyl}-2-oxazoline | $n_D^{26.6}$ 1.5959 |
| (38) 2-(2,6-difluorophenyl)-4-{[4-(2-chloro-4-trifluoromethylphenoxy)phenoxy]methyl}-2-oxazoline | $n_D^{22.8}$ 1.5409 |
| (39) 2-(2,6-difluorophenyl)-4-{[2-chloro-4-(2-chloro-4-trifluoromethylphenoxy)phenoxy]methyl}-2-oxazoline | resinoid |
| (40) 2-(2,6-difluorophenyl)-4-{[4-(4-chlorophenoxy)phenoxy]methyl)-2-oxazoline | $n_D^{23.1}$ 1.5849 |
| (41) 2-(2,6-difluorophenyl)-4-{[4-(2-chloro-4-methoxycarbonylphenoxy)phenoxy]methyl}-2-oxazoline | m.p. 103.1° C. |
| (42) 2-(2,6-difluorophenyl)-4-{[4-(3-chloro-5-trifluoromethylpyrid-2-yloxy)phenoxy]methyl}-2-oxazoline | $n_D^{23.7}$ 1.5298 |
| (43) 2-(2,6-difluorophenyl)-4-{[4-(5-trifluoromethylpyrid-2-yloxy)phenoxy]methyl}-2-oxazoline | $n_D^{23.6}$ 1.5221 |
| (44) 2-(2,6-difluorophenyl)-4-{[3-chloro-4-(3-chloro-5-trifluoromethylpyrid-2-yloxy)phenoxy]methyl}-2-oxazoline | $n_D^{24.6}$ 1.5337 |
| (45) 2-(2,6-difluorophenyl)-4-{[3,5-dichloro-4-(3-chloro-5-trifluoromethylpyrid-2-yloxy)phenoxy]methyl}-2- | resinoid |
| (46) 2-(2,6-difluorophenyl)-4-phenoxymethyl-2-oxazoline | $n_D^{22.4}$ 1.5473 |
| (47) 2-(2,6-difluorophenyl)-4-[(4-methoxyphenoxy)methyl]-2-oxazoline | resinoid |
| (48) 2-(2,6-difluorophenyl)-4-{[4-[(4-chloro-2-methylphenoxy)methyl]phenoxy]methyl}-2-oxazoline | |
| (49) 2-(2,6-difluorophenyl)-4-[(4-benzyl-2,3-dimethylphenoxy)methyl]-2-oxazoline | |
| (50) 2-(2,6-difluorophenyl)-4-{[4-(2-ethoxyethyl)-2-methylphenoxy]methyl}-2-oxazoline | |
| (51) 2-(2,6-difluorophenyl)-4-[(4-benzyl-2-methylphenoxy)methyl]-2-oxazoline | |
| (52) 2-(2-chloro-6-fluorophenyl)-4-{[4-(1,1-dimethylethyl)phenoxy]methyl}-2-oxazoline | |

-continued

(53) 2-(2-chlorophenyl)-4-{[4-(1,1-dimethylethyl)-phenoxy]methyl}-2-oxazoline
(54) 2-(2,6-difluorophenyl)-4-{[4-(4-methoxyphenoxy)-phenoxy]methyl}-2-oxazoline
(55) 2-(2,6-difluorophenyl)-4-{[4-(4-ethylphenoxy)-phenoxy]methyl}-2-oxazoline
(56) 2-(2,6-difluorophenyl)-4-{[4-(4-methoxyphenyl)-phenoxy]methyl}-2-oxazoline
(57) 2-(2,6-difluorophenyl)-4-[(4-benzylphenoxy)methyl]-2-oxazoline
(58) 2-(2,6-difluorophenyl)-4-{[2-methoxy-4-(4-chlorophenyl)phenoxy]methyl}-2-oxazoline Some examples for production of intermediate compounds are shown below.

PRODUCTION EXAMPLE 8

(Production of Intermediate Compound—ether—; Step 1)

To a mixture of 5.33 g (0.133 mol.) of sodium hydride (60%) and 200 ml of anhydrous N,N-dimethylformamide, there was added dropwise a solution of 20.00 g (0.133 mol.) of 4-(1,1-dimethylethyl)phenol in 50 ml of anhydrous N,N-dimethylformamide with stirring at a temperature of from 5° C. to 10° C. for 10 minutes. Then the reaction mixture was stirred at the same temperature for 30 minutes. To the above mixture, there was added dropwise 24.75 g (0.146 mol.) of bromoacetoaldehyde dimethylacetal in 50 ml of anhydrous N,N-dimethylformamide with stirring at the same temperature for 30 minutes. The reaction mixture was then stirred at room temperature for 20 hours. After the reaction was completed, the reaction mixture was poured into water and extracted with ethyl acetate. Then the residue was washed three times with a saturated aqueous solution of ammonium chloride, dried over magnesium sulfate and concentrated under reduced pressure. The residue was subjected to silica gel chromatography to give 30.00 g of 2-[4-(1,1-dimethylethyl)phenoxy]-1,1-dimethoxyethane as a light-yellowish oily substance ($n_D^{22.8}$ 1.4911).

PRODUCTION EXAMPLE 9

(Production of Intermediate Compound—ether—; Step 1)

Following the same procedure with the same molar proportion of materials as in Production Example 8, 2-(4-phenoxyphenoxy)-1,1-dimethoxyethane as a light-yellowish oily substance ($n_D^{22.8}$ 1.5488) was obtained by using 4-phenoxyphenol instead of 4-(1,1-dimethylethyl)phenol.

PRODUCTION EXAMPLE 10

(Production of Intermediate Compound—aldehyde—; Step 2)

To a mixture of 5.00 g (0.021 mol.) of 2-[4-(1,1-dimethylethyl)phenoxy]-1,1-dimethoxyethane and 60 ml of acetic acid, there was added 6 ml of hydrochloric acid (36N) and the reaction mixture was stirred at room temperature for one hour. Then the reaction mixture was poured into 300 ml of cold water and filtrated quickly to recover a resultant white precipitate. The precipitate was obtained as a wet cake of 2-[4-(1,1-dimethylethyl) phenoxy]acetoaldehyde without being dried too much and was quickly used in the next step of the production procedure.

PRODUCTION EXAMPLE 11

(Production of Intermediate Compound—amine—; Step 3)

To a mixture of 2.92 g (54.6 mmol.) of ammonium chloride, 2.47 g (50.4 mmol.) of sodium cyanide and 18 ml (296 mmol.) of a 28% aqueous solution of ammonia, there was added dropwise a solution of the wet cake of 2-[4-(1,1-dimethylethyl)phenoxy]acetoaldehyde obtained in Production Example 9 in 8 ml of methanol with stirring at a temperature of 10° C. for 30 minutes. Then the reaction mixture was further stirred at the same temperature for 30 minutes. Then, the reaction mixture was stirred under an atmosphere of a gas of ammonia at room temperature for 2 days. After the reaction was completed, the resultant mixture was poured into cold water and extracted with ethyl acetate. The residue was washed with water, dried over magnesium sulfate and concentrated under reduced pressure. The residue was subjected to silica gel chromatography to give 3.89 g of 2-amino-3-[4-(1,1-dimethylethyl)-phenoxy]propionitrile as a light-yellowish resinoid [60 MHz $^1$H-NMR (CDCl$_3$, TMS), δ (ppm) 1.26(9H,s), 4.05(2H,d, J=5Hz), 4.63(1H,t, J=5Hz), 6.72(2H,d, J=10Hz), 7.21(2H,d, J=10Hz)].

PRODUCTION EXAMPLE 12

(Production of Intermediate Compound—amine—; Steps 2 and 3)

Following the same procedure with the same molar proportion of materials as in Production Examples 10 and 11, 2-amino-3-(4-phenoxyphenoxy)propionitrile as a light-yellowish solid. (m.p. 76.7° C.) was obtained by using 2-(4-phenoxyphenoxy)acetoaldehyde produced from 2-(4-phenoxyphenoxy)-1,1-dimethoxyethane instead of 2-[4-(1,1-dimethylethyl)phenoxy]acetoaldehyde produced from 2-[4-(1,1-dimethylethyl)-1,1-dimethoxyethane.

PRODUCTION EXAMPLE 13

(Production of Intermediate Compound—amino acid—; Step 4)

To 3.89 g (17.8 mmol.) of 2-amino-3-[4-(1,1-dimethylethyl)phenoxy] propionitrile obtained in Production Example 11, there was added 100 ml of a 5N aqueous solution of hydrochloric acid. The reaction mixture was refluxed by heating with stirring for 10 hours. Then the reaction mixture was cooled to a temperature of 0° C. and filtrated to recover a resultant light-yellowish crystal. After drying, 2.50 g of 2-amino-3-[4-(1,1-dimethylethyl)phenoxy]propionic acid was obtained.

PRODUCTION EXAMPLE 14

(Production of Intermediate Compound—amino alcohol—; Step 5)

To a mixture of 4.00 g (105 mmol.) of lithium aluminum hydride and 50 ml of anhydrous tetrahydrofuran, there was added dropwise a solution of 2.50 g (10.5 mmol.) of 2-amino-3-[4-(1,1-dimethylethyl)phenoxy]-propionic acid obtained in Production Example 13 in 50 ml of anhydrous tetrahydrofuran with stirring under reflux by heating for 30 minutes. Then the reaction mixture was further refluxed by heating with stirring for 2 hours. After the reaction was completed, the resultant mixture was cooled to a temperature of from 5° C. to 10° C. To the resultant mixture, there was added 100 ml of toluene and further added slowly, 10 ml of water and a 5N aqueous solution of sodium hydroxide. The above mixture was dried over anhydrous magnesium sulfate, filtrated with a filter agent (Celite ®) and concentrated under reduced pressure to give 2.10 g of 2-amino-3-[4-(1,1-dimethylethyl)phenoxy]propanol as a light-yellowish solid (m.p. 101.7° C.).

PRODUCTION EXAMPLE 15

(Production of Intermediate Compound—amino alcohol—; Steps 4 and 5)

Following the same procedure with the same molar proportion of materials as in Production Examples 13 and 14, 2-amino-3-(4-phenoxyphenoxy)propanol as a light-yellowish solid (m.p. 61.9° C.) was obtained by using 2-amino-3-(4-phenoxyphenoxy)propionic acid produced from 2-amino-3-(4-phenoxyphenoxy)propionitrile instead of 2-amino-3-[4-(1,1-dimethylethyl)-phenoxy]propionic acid produced from 2-amino-3-[4-(1,1-dimethylethyl)phenoxy]propionitrile.

PRODUCTION EXAMPLE 16

(Production of Intermediate Compound—amide—; Step 11)

To a mixture of 29.11 g (320 mmol.) of 2-amino-1,3-propanediol and 22 ml of pyridine, there was added 1.3 l of dichloromethane with stirring at room temperature. Then, to the above mixture, there was added dropwise 56.2 g (350 mmol.) of 2,6-difluorobenzoylchloride with stirring at the same temperature for 30 minutes. Then the reaction mixture was further stirred at the same temperature for one hour. The resultant mixture was filtrated with a filter glass to remove the resultant precipitate and the filtrate was concentrated under reduced pressure. The residue was subjected to silica gel chromatography to give 7.2 g of N,O-di-(2,6-difluorobenzoyl)-2-amino-1,3-propanediol as a colorless oily substance ($n_D^{24.0}$ 1.5314) and 17.3 g of N,O,O'-tri(2,6-difluorobenzoyl)-2-amino-1,3-propanediol as a colorless oily substance ($n_D^{24.2}$ 1.5169).

PRODUCTION EXAMPLE 17

(Production of Intermediate Compound—haloamide—; Step 13)

A mixture of 5.00 g (17.1 mmol.) of N,O-di(2,6-difluorobenzoyl)-2-amino-1,3-propanediol obtained in Production Example 16 and 15 ml of thionyl chloride was refluxed by heating at a temperature of 80° C. with stirring for one hour. The reaction mixture was cooled to room temperature and concentrated under reduced pressure to give 5.52 g of 2-[N-(2,6-difluorobenzoyl)amino]-3-(2,6-difluorobenzoyloxy)-1-chloropropane as a crude sample.

PRODUCTION EXAMPLE 18

(Production of Intermediate Compound—oxazoline—; Step 14)

To a solution of 5.0 g (13.7 mmol.) of 2-[N(2,6-difluorobenzoyl)amino]-3-(2,6-difluorobenzoyloxy)-1-chloropropane obtained in Production Example 17 in 45 ml of ethanol, there was added slowly 20 ml of a 5% aqueous solution of sodium hydroxide with stirring at a temperature of 70° C. for 5 minutes. Then the reaction mixture was further stirred at the same temperature for 30 minutes. After the reaction was completed, the resultant mixture was cooled to room temperature and concentrated under reduced pressure to remove ethanol. The residue was extracted with ethyl acetate, washed twice with water, dried over anhydrous magnesium sulfate and concentrated under reduced pressure. The residue was subjected to silica gel chromatography to give 2.49 g of 2-(2,6-difluorophenyl)-4-hydroxymethyl-2-oxazoline as a white solid (m.p. 90.4° C.).

PRODUCTION EXAMPLE 19

(Production of Intermediate Compound—amide ester—; Step 21)

To a mixture of 39.0 g (251 mmol.) of D,L-serine methyl ester hydrochloride and 800 ml of pyridine, there was added dropwise 37 ml (324 mmol.) of 2,6-difluorobenzoylchloride with stirring at room temperature for 5 hours. Then the reaction mixture was further stirred at the same temperature for 2 hours. After the reaction was completed, the resultant mixture was concentrated under reduced pressure. To the residue, there was added 500 ml of chloroform. The mixture was washed with water, extracted with chloroform, dried over anhydrous magnesium sulfate and concentrated under reduced pressure. The residue was subjected to silica gel chromatography to give 25.88 g of N-(2,6-difluorobenzoyl)serine methyl ester as a colorless oily substance ($n_D^{22.9}$ 1.5038).

PRODUCTION EXAMPLE 20

(Production of Intermediate Compound—chloroamide ester—; Step 24)

To 25.4 g (98.1 mmol.) of N-(2,6-difluorobenzoyl)serine methyl ester obtained by Production Example 19, there was added 20 ml (274 mmol.) of thionyl chloride at room temperature. The reaction mixture was heated up to a temperature of 80° C. for 5 minutes with stirring and further stirred at a temperature of 80° C. for one hour. After the reaction was completed, the resultant mixture was cooled to room temperature and concentrated under reduced pressure. To the residue, there was added 500 ml of ethyl acetate. The mixture was washed twice with a saturated aqueous solution of sodium bicarbonate, dried over anhydrous magnesium sulfate and concentrated under reduced pressure to give 24.34 g of N-(2,6-difluorobenzoyl)-2-amino-3-chloropropionic acid methyl ester as a white solid (m.p. 93.5° C.).

PRODUCTION EXAMPLE 21

(Production of Intermediate Compound—oxazoline ester—; Step 25)

A mixture of 5.91 g (21.3 mol.) of N-(2,6-difluorobenzoyl)- 2-amino-3-chloropropionic acid methyl ester obtained by Production Example 20, 14.2 g (55.3 mol.) of silver trifluoromethanesulfonate and 120 ml of anhydrous tetrahydrofuran was stirred at room temperature. After the reaction mixture became a colorless solution, the reaction mixture was refluxed by heating with stirring for one hour. After the reaction was completed, the resultant mixture was poured into 300 ml of a saturated aqueous solution of sodium bicarbonate at room temperature. The above mixture was filtrated with a filter agent (celite®) to remove the resultant precipitate, extracted twice with ethyl acetate, dried over anhydrous magnesium sulfate and concentrated under reduced pressure. The residue was subjected to silica gel chromatography to give 4.54 g of 2-(2,6-difluorophenyl)-4-methoxycarbonyl-2-oxazoline as a colorless oily substance ($n_D^{23.2}$ 1.5170).

PRODUCTION EXAMPLE 22

(Production of Intermediate Compound—oxazoline—; Step 23)

A mixture of 0.58 g (15.3 mmol.) of lithium aluminum hydride and 50 ml of anhydrous tetrahydrofuran was refluxed by heating with stirring for 10 minutes. Then the mixture was cooled to a temperature of 0° C. To the mixture, there was added dropwise a solution of 4.54 g (18.8 mmol.) of 2-(2,6-difluorophenyl)-4-methoxycarbonyl-2-oxazoline obtained in Production Example 21 in 13 ml of anhydrous tetrahydrofuran with stirring at a temperature of 0° C. for 20 minutes. Then the reaction mixture was further stirred at the same temperature for 10 minutes. To the resultant mixture, there was added 0.58 ml of water with stirring at the same temperature for 5 minutes. Then the mixture was further stirred at the same temperature for 5 minutes. To the resultant mixture, there was added 0.58 ml of a 30% aqueous solution of potassium hydroxide and further 1.74 ml of water with stirring at the same temperature. After adding, the above mixture was vigorously stirred overnight at room temperature. Then, the mixture was filtrated with a filter glass to remove the resultant precipitate and concentrated under reduced pressure. The residue was subjected to silica gel chromatography to give 3.0 g of 2-(2,6-difluorophenyl)-4-hydroxymethyl-2-oxazoline as a white solid (m.p. 90.4° C.).

PRODUCTION EXAMPLE 23

(Production of optically active intermediate Compounds -oxazoline-)

Following the same procedure with the same molar proportion of materials as in Production Examples 19 to 22, optical active 2-(2,6-difluorophenyl)-4-hydroxymethyl-2-oxazoline is obtained by using D-serine methyl ester hydrochloride instead of D,L-serine methyl ester hydrochloride.

In the same manner as above, the following compounds are obtained.

| | |
|---|---|
| (101) 2-(2,6-difluorophenyl)-4-hydroxymethyl-2-oxazoline | m.p. 90.4° C. |
| (102) 2-(2,6-difluorophenyl)-4-chloromethyl-2-oxazoline | $n_D^{22.6}$ 1.5280 |
| (103) 2-(2,6-difluorophenyl)-4-tosyloxymethyl-2-oxazoline | |
| (104) 2-(2,6-difluorophenyl)-4-mesyloxymethyl-2-oxazoline | |
| (105) 2-(2-chloro-6-fluorophenyl)-4-hydroxymethyl-2-oxazoline | |
| (106) 2-(2-chlorophenyl)-4-chloromethyl-2-oxazoline | |
| (107) 2-(2,6-dichlorophenyl)-4-chloromethyl-2-oxazoline | |
| (108) 2-(2-fluorophenyl)-4-hydroxymethyl-2-oxazoline | |

Next, Formulation Examples are shown, wherein parts are all by weight and the compounds of the present invention are designated by the compound numbers shown above.

FORMULATION EXAMPLE 1

(Emulsifiable Concentrate)

To a solution of 10 parts of each of Compounds Nos. 1 to 58 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

FORMULATION EXAMPLE 2

(Emulsifiable Concentrate)

To a solution of 5 parts of each of Compounds Nos. 1 to 58 and 5 parts of fenpropathrin in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate.

FORMULATION EXAMPLE 3

(Emulsifiable Concentrate)

To a solution of 5 parts of each of Compounds Nos. 1 to 58 and 5 parts of fluvalinate in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate.

FORMULATION EXAMPLE 4

(Emulsifiable Concentrate)

To a solution of 5 parts of each of compounds Nos. 1 to 58 and 5 parts of esfenvalerate in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate.

FORMULATION EXAMPLE 5

(Wettable Powder)

Twenty parts of each of Compounds Nos. 1 to 58 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

FORMULATION EXAMPLE 6

(Wettable Powder)

Ten parts of each of Compounds Nos. 1 to 58 are added to 10 parts of bifenthrin, and the mixture is added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder.

FORMULATION EXAMPLE 7

(Wettable Powder)

Ten parts of each of Compounds Nos. 1 to 58 are added to 10 parts of acrinathrin, and the mixture is added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder.

FORMULATION EXAMPLE 8

(Granules)

Five parts of sodium dodecylbenzenesulfonate, 30 parts of bentonite and 60 parts of clay are added to 5 parts of each of Compounds Nos. 1 to 7, 11, 13, 15, 16, 18, 21, 24 to 26, 36 to 38, 40, 42 to 44 and 46 and the resultant mixture is pulverized and kneaded with a suitable amount of water. The mixture is granulated in a granulator and air-dried to give granules containing the active ingredient in 5%.

FORMULATION EXAMPLE 9

(Granules)

Five parts of fine powder of synthetic hydrated silica, 5 parts of sodium dodecylbenzenesulfonate, 30 parts of bentonite and 55 parts of clay are added to 5 parts of each of Compounds Nos. 10, 14, 17, 19, 23, 27 to 30, 32 to 35 and 41 and the resultant mixture is pulverized and kneaded with a suitable amount of water. The mixture is granulated in a granulator and air-dried to give granules containing the active ingredient in 5%.

FORMULATION EXAMPLE 10

(Dusts)

To a solution of 1 part of each of Compounds Nos. 1 to 58 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give a dust containing the active ingredient in 1%.

FORMULATION EXAMPLE 11

(Flowable Concentrate)

To 40 parts of an aqueous solution containing 2 parts of polyvinyl alcohol, 10 parts of each of Compounds Nos. 1 to 7, 11, 13, 15, 16, 18, 21, 24 to 26, 36 to 38, 40, 42 to 44 and 46 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

FORMULATION EXAMPLE 12

(Flowable Concentrate)

To 40 parts of an aqueous solution containing 2 parts of polyvinyl alcohol, 5 parts of each of Compounds Nos. 1 to 7, 11, 13, 15, 16, 18, 21, 24 to 26, 36 to 38, 40, 42 to 44 and 46 and 5 parts of 2-methyl-2-(4-bromodifluoromethoxyphenyl)propyl (3-phenoxybenzyl)ether are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate.

FORMULATION EXAMPLE 13

(Oil Spray)

Into a mixture of 5 parts of xylene and 5 parts of trichloroethane, 0.1 part of each of Compounds Nos. 1 to 58 is dissolved, and the resultant solution is mixed with 89.9 parts of deodorized kerosene to give an oil spray containing the active ingredient in 0.1%.

FORMULATION EXAMPLE 14

(Oil-based Aerosol)

A solution of 0.1 part of each of Compounds Nos. 1 to 58, 0.2 part of tetramethrin (2,2-dimethyl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

FORMULATION EXAMPLE 15

(Water-based Aerosol)

A solution of 0.2 part of each of Compounds Nos. 1 to 58, 0.2 part of d-allethrin ((2,2-dimethyl-3-(2-methyl-1-propenyl)cyclopropanecarboxylic acid 2-methyl-4-oxo-3-(2-propenyl)-2-cyclopenten-2-yl ester), 0.2 part of d-phenothrin, 5 parts of xylene, 3.4 parts of deodorized kerosene and 1 part of an emulsifier ("ATMOS 300" ®, Atlas Chemical Co., Ltd.) in 50 parts of distilled water is filled in an aerosol container. After provision of a valve, 40 parts of a propellant (liquefied petroleum gas) is filled through the valve under compression to give a water-based aerosol.

FORMULATION EXAMPLE 16

(Fumigant)

Each of Compounds Nos. 1 to 58 (100 mg) is dissolved in an appropriate amount of acetone, and the resultant solution is impregnated into a porous ceramic plate (4.0×4.0×1.2 cm) to give a fumigant.

The following Test Examples show some of the test results which support the controlling effect of the oxazoline derivatives (I) on insects, mites and/or ticks and its resistance to sunlight. The compound numbers correspond to those as shown in the Production Examples. The compounds used for comparison are as follows:

| Compound Symbol | Chemical structure | Remarks |
|---|---|---|
| A | (CH₃)₃C-C₆H₄-CH₂-oxazoline-C₆H₃F₂ | Compound disclosed in European Patent No. 345,775 |
| B | C₆H₅-O-C₆H₄-CH₂-oxazoline-C₆H₃F₂ | Compound disclosed in European Patent No. 432,661 |

TEST EXAMPLE 1

(Insecticidal Test on Common Mosquito)

The emulsifiable concentrate of the test compound prepared according to Formulation Example 1 was diluted with water and 0.7 ml of the dilution was added to 100 ml of ion exchange water (concentration of the effective ingredient was 3.5 ppm). In the mixture were released 20 last instar larvae of common mosquito (*Culex pipiens pallens*). The larvae were bred on a bait until emergence to obtain an inhibitory ratio of the emergence.

Criterion for the judgement is as follows.
a: 90% or more
b: not less than 80% but less than 90%
c: less than 80%

As the results, compounds Nos. 1, 4, 5, 6, 7, 10, 11, 12, 13, 14, 15, 16, 17, 18, 19, 20, 22, 24, 25, 26, 27, 28, 29, 30, 36, 37, 38, 40, 41, 42, 43 and 44 showed "a" at a concentration of 3.5 ppm. On the other hand, compound A and B each showed "b" at the same concentration as above and no treatment showed "c".

TEST EXAMPLE 2

Insecticidal Ttest on Tobacco Cutworm (*Spodoptera litura*)

Each test compound was formulated into an emulsifiable concentrate according to Formulation Example 1, and 2 ml of the aqueous dilute solution (500 ppm) of the emulsifiable concentrate was impregnated into 13 g of artificidal feeds for tobacco cutworm previously prepared in a polyethylene cup of 11 cm in diameter. Ten fourth instar larvae of tobacco cutworm were liberated in the cup. After six days, the larvae were examined to obtain a mortality. As the results, compounds Nos. 11, 13, 15, 24, 25, 26, 28, 29, 30, 38, 39, 43 and 44 showed 100% at a concentration of 500 ppm. On the other hand, compound A and B showed 0% and 20% respectively and no treatment showed 0%.

TEST EXAMPLE 3

Insecticidal Test Against Diamondback moths (*Plutella xylostella*)

An emulsifiable concentrate of a test compound formulated according to the Formulation Example 1 was diluted with water to make an emulsion (corresponding to 50 ppm concentration).

Each two radish seedlings (5-6 days after sowing), laid no eggs and about 100 to 150 eggs of diamondback moths were immersed in the emulsion for 30 seconds, then air-dried for about one hour. The treated seedlings were placed in a .polyethylene cup of 5.5 cm diameter. After 5 days, the number of larvae after hatching was counted to obtain an egg-mortality.

Criterion for the judgement is as follows.
a: 100%
b: not less than 90%, but less than 99%,
c: less than 90%.

As the results, compounds Nos. 10, 11, 12, 13, 14, 17, 25, 26, 27, 28, 30, 42 and 44 showed "a". On the other hand, compound A and B showed "c" each and no treatment showed each "c" and no treatment showed "c".

TEST EXAMPLE 4

(Acaricidal Test on Carmine Spider Mite (*Tetranychus cinnabarius*)

Female adult carmine spider mites were parasitized, at a rate of 10 adults per leaf, on a potted kidney bean plant (in the primary leaf stage, 7 days after seeding), and placed in a room which was kept at a temperature of 25° C. After 6 days, the emulsifiable concentrate of each test compound prepared according to Formulation Example 1 was diluted with water to an active ingredient concentration of 500 ppm, and the dilute solution was sprayed onto the plant at a rate of 15 ml per pot on a turn table. At the same time, the soil was drenched with 2 ml of the same dilute solution. After 8 days, the degree of damage to each plant by the mites was examined. The efficacy was judged according to the following criteria:

−: Almost no damage was observed,
+: Slight damage was observed,
++: Same damage as that of the untreated pot was observed.

As the results, compounds Nos. 1, 2, 4, 5, 6, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46 and 47 showed "−". On the other hand, compound A showed "++" and no treatment showed "++".

TEST EXAMPLE 5

Resistance Test Against the Direct Radiation of Sunlight

A solution of 10 mg of the test compound in 3 ml of methylene chloride was spread on a glass petri dish of 8 cm diameter. After the petri dish was air-dried, the petri dish was set in the direct radiation of the sunlight only during the day and not on rainy days. After a total time of 37 hours on 8 days, the test compound was recovered from the petri dish with 5 ml of dichloromethane and measured by high performance liquid chromatography (HPLC);

carrier solvent: a mixture of acetonitrile and water (7:3 or 8:2)
column: ODS
flow rate: 1.0 ml/min
detector UV: (254 nm)

As the result, compounds Nos. 1, 13 and 36 showed 94.9%, 95.3% and 87.9%, respectively, as a ratio of the residue. On the other hand, compound A showed only 14.6% as a ratio of the residue.

What is claimed is:

1. An oxazoline derivative having the formula:

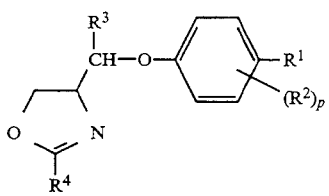
(I)

wherein $R^1$ is a hydrogen atom, a halogen atom, a $C_1$-$C_{16}$ alkyl group, a $C_1$-$C_{16}$ haloalkyl group, an alkoxyalkyl group having 2 to 16 carbon atoms, a $C_1$-$C_{16}$ alkoxy group, a $C_1$-$C_{16}$ haloalkoxy group, a $C_1$-$C_{16}$ alkylthio group, a $C_1$-$C_{16}$ haloalkylthio group, a $C_1$-$C_{10}$ cycloalkyl group, a $C_3$-$C_{10}$ halocycloalkyl group, an alkylcycloalkyl group having 4 to 10 carbon atoms, a $C_5$-$C_{10}$ cycloalkoxy group, a $C_5$-$C_{10}$ halocycloalkoxy group, an alkylcycloalkoxy group having 5 to 10 carbon atoms or a group of the formula:

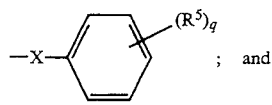
; and (wherein $R_5$ is, the same or different, a hydrogen atom, a halogen atom, a $C_1$-$C_8$ alkyl group, a $C_1$-$C_8$ haloalkyl group, an alkoxyalkyl group having 2 to 8 carbon atoms, a $C_1$-$C_8$ alkoxy group, a $C_1$-$C_8$ haloalkoxy group, a $C_1$-$C_8$ alkylthio group or a $C_1$-$C_8$ haloalkylthio group; X is a single bond, an oxygen atom, a sulfur atom, a methylene group or a methyleneoxy group (—$CH_2O$—, —$OCH_2$—); q is an integer of 1 to 5); $R^2$ is a hydrogen atom, a halogen atom, a $C_1$-$C_3$ alkyl group, a $C_1$-$C_3$ alkoxy group or a $C_1$-$C_3$ alkylthio group; p is an integer of 1 to 4; $R^3$ is a hydrogen atom or a methyl group; $R^4$ is a group of the formula:

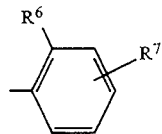

(wherein $R^6$ and $R^7$ may be the same or different, and each of which is a hydrogen atom, a halogen atom, a $C_1$-$C_3$ alkyl group, a $C_1$-$C_3$ haloalkyl group, a $C_1$-$C_3$ alkoxyl group or a $C_1$-$C_3$ haloalkoxy group).

2. The oxazoline derivative according to claim 1, wherein $R^1$ is a hydrogen atom, a halogen atom, a $C_1$-$C_{16}$ alkyl group, a $C_1$-$C_{16}$ haloalkyl group, an alkoxyalkyl group having 2 to 16 carbon atoms, a $C_1$-$C_{16}$ alkoxy group, a $C_1$-$C_{16}$ haloalkoxy group, a $C_1$-$C_{16}$ alkylthio group, a $C_1$-$C_{16}$ haloalkylthio group, a $C_1$-$C_{16}$ cycloalkyl group, a $C_3$-$C_{10}$ halocycloalkyl group, an alkylcycloalkyl group having 4 to 10 carbon atoms, a $C_5$-$C_{10}$ cycloalkoxy group, a $C_5$-$C_{10}$ halocycloalkoxy group, an alkylcycloalkoxy group having 5 to 10 carbon atoms or a group of the formula:

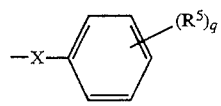

(wherein $R^5$ is, the same or different, a hydrogen atom, a halogen atom, a $C_1$-$C_8$ alkyl group, a $C_1$-$C_8$ haloalkyl group, an alkoxyalkyl group having 2 to 8 carbon atoms, a $C_1$-$C_8$ alkoxy group, a $C_1$-$C_8$ haloalkoxy group, a $C_1$-$C_8$ alkylthio group or a $C_1$-$C_8$ haloalkylthio group; X is a single bond, an oxygen atom, a sulfur atom or a methylene group; q is an integer of 1 or 2); $R^2$ is a hydrogen atom, a halogen atom, a $C_1$-$C_3$ alkyl group, a $C_1$-$C_3$ alkoxy group or a $C_1$-$C_3$ alkylthio group; p is an integer of 1 or 2; $R^3$ is a hydrogen atom or a methyl group; $R^4$ is a group of the formula:

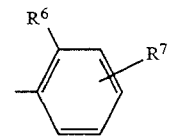

(wherein $R^6$ and $R^7$ may be the same or different, and each of which is a hydrogen atom, a halogen atom, a $C_1$-$C_3$ alkyl group, a $C_1$-$C_3$ haloalkyl group, a $C_1$-$C_3$ alkoxyl group or a $C_1$-$C_3$ haloalkyl group).

3. The oxazoline derivative according to claim 1, wherein $R^1$ is a hydrogen atom, a $C_1$-$C_{16}$ alkyl group, an alkoxyalkyl group having 2 to 16 carbon atoms, a $C_1$-$C_{16}$ alkoxy group, a $C_1$-$C_{16}$ haloalkylthio group, a $C_3$-$C_{10}$ cycloalkyl group or a group of the formula:

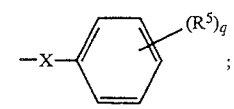

(wherein $R^5$ is, the same or different, a hydrogen atom, a halogen atom, a $C_1$-$C_8$ alkyl group, a $C_1$-$C_8$ haloalkyl group, a $C_1$-$C_8$ alkoxy group, a $C_1$-$C_8$ haloalkoxy group or a $C_1$-$C_8$ alkylthio group; X is a single bond, an oxygen atom or a methylene group; Y is a methine (—CH═) group or a nitrogen atom; q is an integer of 1 or 2; $R^2$ is a hydrogen atom, a halogen atom, a $C_1$-$C_3$ alkyl group or a $C_1$-$C_3$ alkoxy group; p is an integer of 1 to 3; $R^3$ is a hydrogen atom; $R^4$ is a group of the formula:

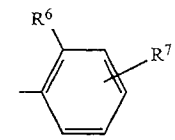

(wherein $R^6$ and $R^7$ may be the same or different, and each of which is a halogen atom).

4. The oxazoline derivative according to claim 1, wherein $R^1$ is a group of the formula:

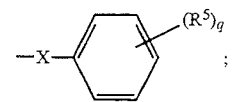

(wherein $R^5$ is, the same or different, a hydrogen atom, a halogen atom, a $C_1$-$C_8$ alkyl group, a $C_1$-$C_8$ haloalkyl group, an alkoxyalkyl group having 2 to 8 carbon atoms, a $C_1$-$C_8$ alkoxy group, a $C_1$-$C_8$ haloalkoxy group, a $C_1$-$C_8$ alkylthio group or a $C_1$-$C_8$ haloalkylthio group; X is a single bond, an oxygen atom, a sulfur atom, a methylene group or a methyleneoxy group (—CH₂O—, —OCH₂—); q is an integer of 1 to 5).

5. The oxazoline derivative according to claim 1, wherein R¹ is a group of the formula:

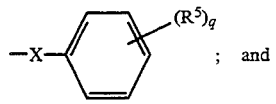
; and (wherein R⁵ is a hydrogen atom, a halogen atom, a C₁–C₈ alkyl group, a C₁–C₈ haloalkyl group, a C₁–C₈ alkoxy group or a C₁–C₈ haloalkoxy group at the p-position to the substituent "X"; X is a single bond or an oxygen atom; q is one).

6. The oxazoline derivative according to claim 1, which is 2-(2,6-difluorophenyl)-4-[(4-n-heptylphenoxy)-methyl]-2-oxazoline.

7. The oxazoline derivative according to claim 1, which is 2-(2,6-difluorophenyl)-4-{[3,5-dimethyl-4-(4-chlorophenyl)phenoxy]methyl}-2-oxazoline.

8. The oxazoline derivative according to claim 1, which is 2-(2,6-difluorophenyl)-4-{[3,5-dimethyl-4-(4-ethylphenyl)phenoxy]methyl}-2-oxazoline.

9. The oxazoline derivative according to claim 1, which is 2-(2,6-difluorophenyl)-4-{[4-(4-chloro-2-methylphenyl)phenoxy]methyl}-2-oxazoline.

10. The oxazoline derivative according to claim 1, which is 2-(2,6-difluorophenyl)-4-{[4-(4-trifluoromethylphenyl)phenoxy] methyl}-2-oxazoline.

11. The oxazoline derivative according to claim 1, 2-(2,6-difluorophenyl)-4-{[4-(4-trifluoromethoxyphenyl) phenoxy]methyl}-2-oxazoline.

12. The oxazoline derivative according to claim 1, 2-(2,6-difluorophenyl)-4-{[4-(2-chloro-4-trifluoromethylphenoxy)phenoxy]methyl}-2-oxazoline.

13. The oxazoline derivative according to claim 1, which is 2-(2,6-difluorophenyl)-4-{[2-chloro-4-(2-chloro-4-trifluoromethylphenoxy)phenoxy]methyl}-2-oxazoline.

14. The oxazoline derivative according to claim 1, which is 2-(2,6-difluorophenyl)-4-[(4-benzyl-2-methylphenoxy)methyl]-2-oxazoline.

15. The oxazoline derivative according to claim 1, which is 2-(2-chloro-6-fluorophenyl)-4-{[4-(1,1-dimethylethyl)phenoxy]methyl}-2-oxazoline.

16. The oxazoline derivative according to claim 1, which is 2-(2-chlorophenyl)-4-{[4-(1,1-dimethylethyl)phenoxy]methyl}-2-oxazoline.

17. An insecticidal and/or acaricidal composition which comprises an insecticidally and/or acaricidally effective amount of the oxazoline derivative according to claim 1 and an inert carrier.

18. A method for controlling insects, mites and/or ticks which comprises applying an insecticidally and/or acaricidally effective amount of the oxazoline derivative according to claim 1 to the insects, mites and/or ticks or to the locus where the insects, mites and/or ticks propagate.

* * * * *